United States Patent
Nishibayashi et al.

(10) Patent No.: US 10,292,604 B2
(45) Date of Patent: May 21, 2019

(54) AUTOMATIC BLOOD PRESSURE MEASUREMENT DEVICE

(71) Applicants: Hideo Nishibayashi, Kitamoto (JP); Kazuya Sata, Kitamoto (JP)

(72) Inventors: Hideo Nishibayashi, Kitamoto (JP); Kazuya Sata, Kitamoto (JP)

(73) Assignee: A&D COMPANY, LIMITED, Tokyo (JP)

( * ) Notice: Subject to any disclaimer, the term of this patent is extended or adjusted under 35 U.S.C. 154(b) by 493 days.

(21) Appl. No.: 14/382,730

(22) PCT Filed: Mar. 5, 2013

(86) PCT No.: PCT/JP2013/056037
§ 371 (c)(1),
(2) Date: Sep. 3, 2014

(87) PCT Pub. No.: WO2013/133289
PCT Pub. Date: Sep. 12, 2013

(65) Prior Publication Data
US 2015/0025399 A1    Jan. 22, 2015

(30) Foreign Application Priority Data
Mar. 6, 2012    (JP) ................................ 2012-049799

(51) Int. Cl.
*A61B 5/022*    (2006.01)
*A61B 5/021*    (2006.01)
*A61B 5/02*    (2006.01)

(52) U.S. Cl.
CPC ...... *A61B 5/02233* (2013.01); *A61B 5/02116* (2013.01); *A61B 5/02141* (2013.01);
(Continued)

(58) Field of Classification Search
CPC ....... A61B 5/02; A61B 5/02116; A61B 5/021; A61B 5/022; A61B 5/02233
See application file for complete search history.

(56) References Cited

U.S. PATENT DOCUMENTS

| 5,323,782 A | 6/1994 | Shirasaki et al. |
| 5,564,426 A | 10/1996 | Iwai |
| (Continued) |

FOREIGN PATENT DOCUMENTS

| CN | 101340845 A | 1/2009 |
| EP | 1 388 319 A1 | 2/2004 |
| (Continued) |

OTHER PUBLICATIONS

Aug. 28, 2015 Office Action issued in Chinese Patent Application No. 201380012303.9.
(Continued)

*Primary Examiner* — Puya Agahi
(74) *Attorney, Agent, or Firm* — Oliff PLC

(57) ABSTRACT

An automatic blood pressure measuring apparatus includes: a compression band wrapped around a compressed site of a living body, the automatic blood pressure measuring apparatus sequentially extracting a pulse wave that is pressure oscillation in the compression band in a process of changing a compression pressure value of the compression band to determine a blood pressure value of the living body based on a change in the pulse wave, the compression band having a plurality of expansion bags having independent air chambers aligned in a width direction to respectively compress the compressed site of the living body, the automatic blood pressure measuring apparatus sequentially calculating an amplitude ratio of an amplitude value of a pulse wave from a predetermined expansion bag positioned on a downstream side of an upstream expansion bag positioned on an
(Continued)

upstream side of an artery in the compressed site out of the expansion bags.

6 Claims, 15 Drawing Sheets

(52) U.S. Cl.
CPC .................. *A61B 5/02* (2013.01); *A61B 5/021* (2013.01); *A61B 5/022* (2013.01)

(56) References Cited

U.S. PATENT DOCUMENTS

| | | | |
|---|---|---|---|
| 2002/0002340 | A1 | 1/2002 | Nishibayashi |
| 2004/0024325 | A1* | 2/2004 | Nishibayashi ..... A61B 5/02225 600/492 |
| 2009/0312651 | A1 | 12/2009 | Sano et al. |
| 2011/0160599 | A1 | 6/2011 | Kobayashi et al. |

FOREIGN PATENT DOCUMENTS

| | | |
|---|---|---|
| JP | A-58-22029 | 2/1983 |
| JP | A-61-122840 | 6/1986 |
| JP | H04261639 A | 9/1992 |
| JP | A-05-269089 | 10/1993 |
| JP | H06-70894 A | 3/1994 |
| JP | H07227382 A | 8/1995 |
| JP | H08332171 A | 12/1996 |
| JP | 2000-237151 A | 9/2000 |
| JP | A-2001-333888 | 12/2001 |
| JP | A-2007-044363 | 2/2007 |
| JP | 2007-098003 A | 4/2007 |

OTHER PUBLICATIONS

Aug. 16, 2016 Office Action issued in Japanese Patent Application No. 2012-049799.
Apr. 9, 2013 International Search Report issued in International Application No. PCT/JP2013/056037.
Apr. 5, 2016 Office Action issued in Japanese Patent Application No. 2012-049799.
Aug. 14, 2015 Extended Search Report issued in European Application No. 13758330.8.
Jul. 25, 2017 Office Action issued in Japanese Application No. 2016-220002.
Dec. 11, 2017 Office Action issued in Eureopen Patent Application No. 13758330.8.
Jun. 21, 2018 Office Action issued in European Patent Application No. 13758330.8.

* cited by examiner

US 10,292,604 B2

AUTOMATIC BLOOD PRESSURE MEASUREMENT DEVICE

TECHNICAL FIELD

The present invention relates to an automatic blood pressure measuring apparatus including a compression band wrapped around a compressed site that is a limb of a living body such as an arm and an ankle and particularly to a technique of determining a maximum blood pressure of a living body based on a pulse wave signal acquired from the compression band.

BACKGROUND ART

An automatic blood pressure measuring apparatus is known that includes a compression band wrapped around a compressed site of a living body and that sequentially extracts a pulse wave that is pressure oscillation in the compression band in the process of changing a compression pressure value of the compression band to determine a blood pressure value of the living body based on a change in the pulse wave. Since an expansion bag included in the compression band needs a sufficiently large compression width dimension relative to a diameter of a compressed site and has a relatively large capacity, the pulse wave, i.e., the pressure oscillation, generated in response to a change in capacity of an artery in the compressed site tends to be a weak signal and therefore causes reduction in measurement accuracy.

In this regard, as described in Patent Document 1, to clearly detect a change in capacity of an artery, a two-layer structure compression band is proposed and the compression band is disposed with a detection expansion bag having a capacity smaller than a main expansion bag such that the entire bag overlaps in the width direction with a portion of inside of the main expansion bag, and has a shield plate disposed between the detection expansion bag and the main expansion bag. According to this compression band, while a portion of the main expansion bag directly pressurizes a compressed site, another portion of the main expansion bag pressurizes the compressed site indirectly through the detection expansion bag.

PRIOR ART DOCUMENT

Patent Document

Patent Document 1: Japanese Laid-Open Patent Publication No. 5-269089

SUMMARY OF THE INVENTION

Problem to be Solved by the Invention

However, since an automatic blood pressure measuring apparatus including the conventional two-layer structure compression band described in Patent Document 1 has the detection expansion bag located toward skin of a living body and therefore cannot properly apply the pressure of the main expansion bag to an artery, the automatic blood pressure measuring apparatus is disadvantageous in that a correct pulse wave is hardly acquired and that an accuracy of the maximum blood pressure value determined based on the pulse wave is poor.

It is therefore an object of the present invention to provide an automatic blood pressure measuring apparatus capable of determining a highly accurate maximum blood pressure value based on a pulse wave acquired at the time of compression of an artery in a compressed site of a living body.

Means for Solving the Problem

In view of the situations, the present inventor experimentally produced a compression band having a plurality of air chambers aligned in the width direction to independently compress a compressed site of a living body, for example, a triple cuff having three air chambers, and comparatively studied respective cuff pulse waves acquired independently from the three air chambers to discover the following fact. Specifically, during an ischemic state associated with a high cuff pressure, a pulse wave generated in an air chamber on the most upstream side is propagated through physical interference (crosstalk) to an adjacent air chamber and an interference pulse wave attenuated at a predetermined attenuation rate is generated in an adjacent intermediate air chamber and a downstream air chamber; however, when a cuff pressure becomes lower and a blood flow is started, a volume pulse wave generated by a volume change due to the blood flow is generated in the intermediate air chamber and the downstream air chamber, including the interference pulse wave. Although the amplitude of the volume pulse wave tends to be slightly larger than the interference pulse wave, it is difficult to stably identify the pulse waves only from an amplitude difference indicative of the tendency. Therefore, by using a variable that is an amplitude ratio of the pulse wave generated in the intermediate air chamber or the downstream air chamber to the pulse wave generated in the upstream air chamber, it was discovered that, although substantially constant during the ischemic state associated with a high cuff pressure, the amplitude ratio has a property of abruptly rising when a cuff pressure becomes lower and a blood flow is started, and it was found out that the cuff pressure at the time of judgment of the abrupt rise can accurately be determined as the maximum blood pressure value of the living body. The present invention was conceived based on this knowledge.

Therefore, the first aspect of the invention provides (a) an automatic blood pressure measuring apparatus comprising: a compression band wrapped around a compressed site of a living body, the automatic blood pressure measuring apparatus sequentially extracting a pulse wave that is pressure oscillation in the compression band in a process of changing a compression pressure value of the compression band to determine a blood pressure value of the living body based on a change in the pulse wave, (b) the compression band having a plurality of expansion bags having independent air chambers aligned in a width direction to respectively compress the compressed site of the living body, (c) the automatic blood pressure measuring apparatus sequentially calculating an amplitude ratio of an amplitude value of a pulse wave from a predetermined expansion bag positioned on a downstream side of an upstream expansion bag positioned on an upstream side of an artery in the compressed site out of the plurality of the expansion bags to an amplitude value of a pulse wave from the upstream expansion bag, the automatic blood pressure measuring apparatus determining a maximum blood pressure value of the living body based on that the amplitude ratio exceeds a preset amplitude ratio change judgment value, wherein (d) an amplitude value of a pulse wave from the upstream expansion bag and an amplitude value of a pulse wave from the downstream expansion bag are sequentially acquired in periods within one pulse of the living body and shorter than a period of the pulse, and wherein (e) the amplitude ratios are sequentially calculated in periods shorter than the period of the pulse from the amplitude value of the pulse wave from the upstream expansion bag and the amplitude value of the pulse wave from the downstream expansion bag sequentially acquired in periods shorter than the period of the pulse.

The second aspect of the invention provides the automatic blood pressure measuring apparatus recited in the first aspect of the invention, wherein the compression band has a pair of an upstream expansion bag and a downstream expansion bag comprised of flexible sheets positioned across a predetermined distance in a longitudinal direction of the compressed site, and an intermediate expansion bag disposed between the upstream expansion bag and the downstream expansion bag to align in the longitudinal direction of the compressed site, and wherein the intermediate expansion bag has an air chamber independent of the upstream expansion bag and the downstream expansion bag.

The third aspect of the invention provides the automatic blood pressure measuring apparatus recited in the second aspect of the invention, wherein in a process of reducing a compression pressure value of the pressurized compression band while the compressed site is compressed at the same pressures by the upstream expansion bag, the intermediate expansion bag, and the downstream expansion bag, when a preset first amplitude ratio change judgment value is exceeded by a first amplitude ratio that is a value acquired by dividing an amplitude value of a pulse wave from the intermediate expansion bag by an amplitude value of a pulse wave from the upstream expansion bag and a preset second amplitude ratio change judgment value is exceeded by a second amplitude ratio that is a value acquired by dividing an amplitude value of a pulse wave from the downstream expansion bag by the amplitude value of the pulse wave from the intermediate expansion bag, the maximum blood pressure value of the living body is determined based on a compression pressure value of the intermediate expansion bag.

The fourth aspect of the invention provides the automatic blood pressure measuring apparatus recited in the second aspect of the invention, wherein in a process of reducing a compression pressure value of the pressurized compression band while the compressed site is compressed at the same pressures by the upstream expansion bag, the intermediate expansion bag, and the downstream expansion bag, when a preset third amplitude ratio change judgment value is exceeded by a third amplitude ratio that is a value acquired by dividing an amplitude value of a pulse wave from the downstream expansion bag by an amplitude value of a pulse wave from the upstream expansion bag, the maximum blood pressure value of the living body is determined based on a compression pressure value of the intermediate expansion bag.

The fifth aspect of the invention provides the automatic blood pressure measuring apparatus recited in any one of the first to fourth aspects of the invention, comprising pressure sensors detecting pressure in the plurality of the expansion bags, wherein after a compression pressure value of the plurality of the expansion bags of the compression band wrapped around the compressed site is increased to a value sufficient for stopping a blood flow of an artery in the compressed site, in a process of reducing the compression pressure value of the compression band, the automatic blood pressure measuring apparatus retains the compression pressure value of the compression band for a predetermined time each time a predetermined amount of pressure is gradually reduced and detects a pulse wave that is pressure oscillation in the compression band within the predetermined time.

Effects of the Invention

According to the automatic blood pressure measuring apparatus recited in the first aspect of the invention, the compression band has a plurality of expansion bags having independent air chambers aligned in a width direction to respectively compress the compressed site of the living body, the automatic blood pressure measuring apparatus sequentially calculates an amplitude ratio of an amplitude value of a pulse wave from a expansion bag positioned on a downstream side of an upstream expansion bag positioned on an upstream side of an artery in the compressed site out of the plurality of the expansion bags to an amplitude value of a pulse wave from the upstream expansion bag, the automatic blood pressure measuring apparatus determines a maximum blood pressure value of the living body based on that the amplitude ratio exceeds a preset amplitude ratio change judgment value. Therefore, since the respective correct pulse waves are acquired from each of the expansion bags by applying the compression pressure to the artery in the compressed site of the living body in uniform pressure distribution from the plurality of the expansion bags put into a mutually independent state in terms of pressure variation, the highly accurate maximum blood pressure value is acquired based on the amplitude ratios between the pulse waves. Since the amplitude ratios have the property of abruptly increasing when the compression pressure of the compression band nearly reaches the maximum blood pressure value of the living body, the highly accurate maximum blood pressure value can be acquired by judging the abrupt increase by using the amplitude ratio change judgment values Further, since an amplitude value of a pulse wave from the upstream expansion bag and an amplitude value of a pulse wave from the downstream expansion bag are sequentially acquired in periods within one pulse of the living body and shorter than a period of the pulse, and the amplitude ratios are sequentially calculated in periods shorter than the period of the pulse from the amplitude value of the pulse wave from the upstream expansion bag and the amplitude value of the pulse wave from the downstream expansion bag sequentially acquired in periods shorter than the period of the pulse, the highly accurate maximum blood pressure value is acquired, based on the amplitude ratios sequentially obtained within one pulse, by judging the abrupt increase thereof by using the amplitude ratio change judgment values.

According to the automatic blood pressure measuring apparatus recited in the second aspect of the invention, since the compression band has a pair of an upstream expansion bag and a downstream expansion bag comprised of flexible sheets positioned across a predetermined distance in a longitudinal direction of the compressed site, and an intermediate expansion bag disposed between the upstream expansion bag and the downstream expansion bag to align in the longitudinal direction of the compressed site, the intermediate expansion bag has an air chamber independent of the upstream expansion bag and the downstream expansion bag, correct pulse waves are acquired by applying the compression pressure to the artery in the compressed site of the living body in uniform pressure distribution from the upstream expansion bag, the intermediate expansion bag, and the downstream expansion bag aligning in the longitudinal direction of the compressed site and put into a mutually independent state in terms of pressure variation and, therefore, the highly accurate maximum blood pressure value is acquired based on the amplitude ratios between the pulse waves.

According to the automatic blood pressure measuring apparatus recited in the third aspect of the invention, in a process of reducing a compression pressure value of the pressurized compression band while the compressed site is compressed at the same pressures by the upstream expansion bag, the intermediate expansion bag, and the downstream expansion bag, when a preset first amplitude ratio change judgment value is exceeded by a value acquired by dividing an amplitude value of a pulse wave from the intermediate expansion bag by an amplitude value of a pulse wave from the upstream expansion bag and/or a preset second amplitude ratio change judgment value is exceeded by a value acquired by dividing an amplitude value of a pulse wave from the downstream expansion bag by the amplitude value of the pulse wave from the intermediate expansion bag, a compression pressure value of the intermediate expansion bag is determined as the maximum blood pressure value of the living body. Therefore, discrimination is made between a state in which the blood flow of the artery in the compressed site passes under the upstream expansion bag and does not pass under the intermediate expansion bag and/or under the downstream expansion bag and a state in which the blood flow of the artery in the compressed site passes under both the predetermined expansion bag and the downstream expansion bag and, when the blood flow of the artery in the compressed site starts passing under the upstream expansion bag and under both the intermediate expansion bag and/or the downstream expansion bag, the compression pressure value of the compression band is determined as the maximum blood pressure value of the living body and, thus, the highly accurate maximum blood pressure value is acquired.

According to the automatic blood pressure measuring apparatus recited in the fourth aspect of the invention, in a process of reducing a compression pressure value of the pressurized compression band while the compressed site is compressed at the same pressures by the upstream expansion bag, the intermediate expansion bag, and the downstream expansion bag, when a preset third amplitude ratio change judgment value is exceeded by a value acquired by dividing an amplitude value of a pulse wave from the downstream expansion bag by an amplitude value of a pulse wave from the upstream expansion bag, a compression pressure value of the intermediate expansion bag is determined as the maximum blood pressure value of the living body. Therefore, discrimination is made between a state in which the blood flow of the artery in the compressed site passes under the upstream expansion bag and does not pass under the downstream expansion bag and a state in which the blood flow of the artery in the compressed site passes under both the upstream expansion bag and the downstream expansion bag and, when the blood flow of the artery in the compressed site starts passing under the upstream expansion bag and the downstream expansion bag, the compression pressure value of the intermediate expansion bag in uniform pressure distribution in the width direction is determined as the maximum blood pressure value of the living body and, thus, the highly accurate maximum blood pressure value is acquired.

According to the automatic blood pressure measuring apparatus recited in the fifth aspect of the invention, the automatic blood pressure measuring apparatus comprises pressure sensors detecting pressure in the plurality of the expansion bags, and after a compression pressure value of the plurality of the expansion bags of the compression band wrapped around the compressed site is increased to a value sufficient for stopping a blood flow of an artery in the compressed site, in a process of reducing the compression pressure value of the compression band, the automatic blood pressure measuring apparatus retains the compression pressure value of the compression band for a predetermined time each time a predetermined amount of pressure is gradually reduced and detects a pulse wave that is pressure oscillation in the compression band within the predetermined time. Therefore, since the pulse waves are detected when the compression pressure values are constant, the correct pulse waves can be acquired. If a plurality of pulse waves are detected within the predetermined time and the maximum blood pressure value is determined based on an average value of the plurality of the pulse waves, the more highly accurate maximum blood pressure value is acquired.

MODE FOR CARRYING OUT THE INVENTION

An example of the present invention will now be described in detail with reference to the drawings. In the following example, the figures are simplified or deformed as needed and portions are not necessarily precisely depicted in terms of dimension ratio, shape, etc.

EXAMPLE

Figure 1:
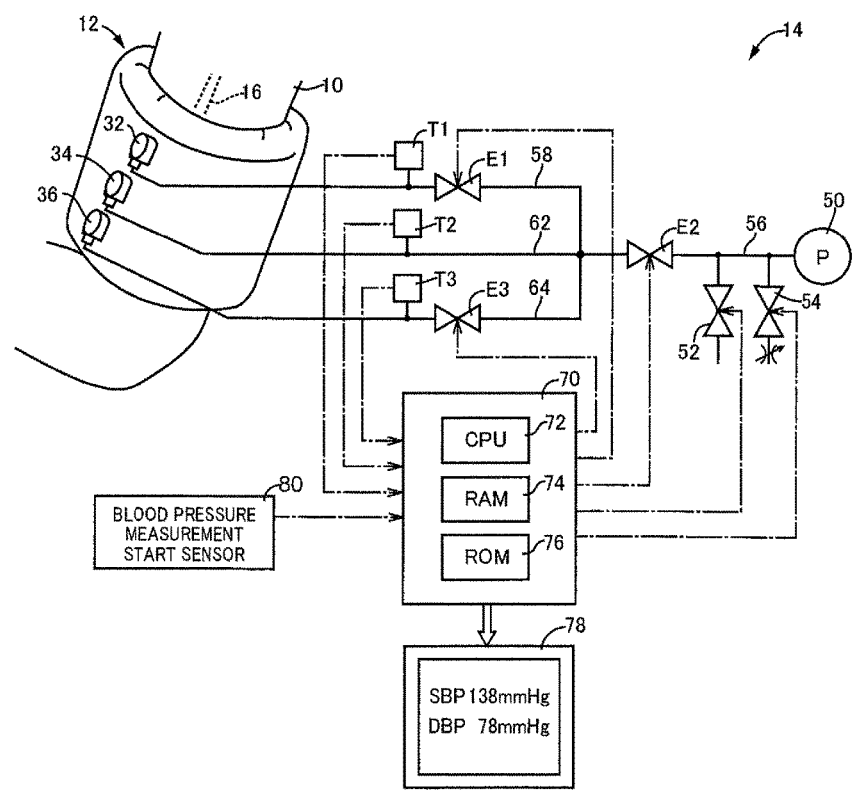
FIG. 1 depicts an automatic blood pressure measuring apparatus that is an example of the present invention including a compression band for an upper arm wrapped around an upper arm that is a compressed site of a living body.

FIG. 1 depicts an automatic blood pressure measuring apparatus 14 that is an example of the present invention including a compression band 12 for an upper arm wrapped around a living body's limb that is a compressed site, for example, an upper arm 10. The automatic blood pressure measuring apparatus 14 sequentially extracts a pulse wave (see FIGS. 6 to 11 described later) that is pressure oscillation in the compression band 12 generated in response to a change in capacity of an artery 16 in the process of reducing a compression pressure of the compression band 12 increased to a value sufficient for stopping a blood flow of the artery 16 in the upper arm 10 and measures a maximum blood pressure value SBP and a minimum blood pressure value DBP of the living body based on a change in the pulse wave.

Figure 2:
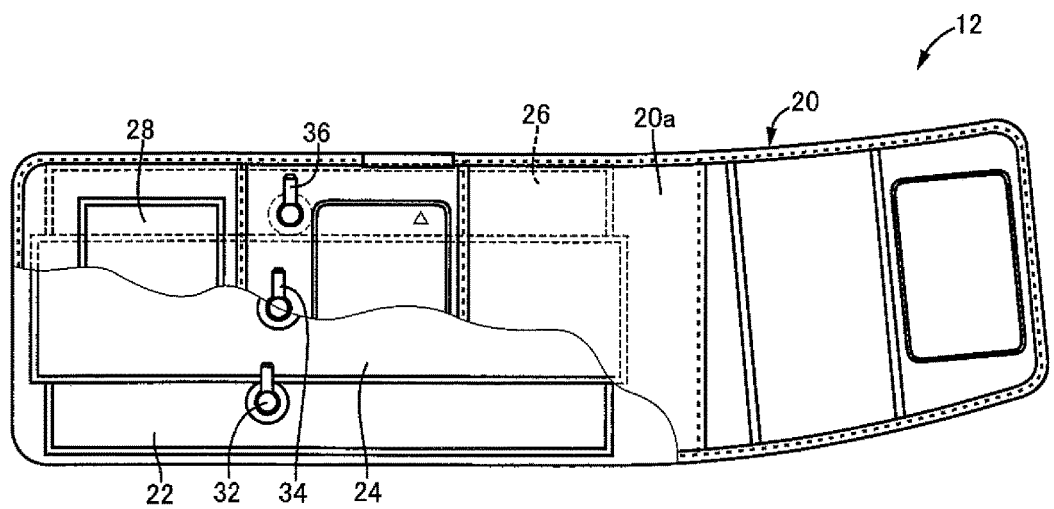
FIG. 2 is a partially cutaway view of an outer circumferential surface of the compression band of FIG. 1.

FIG. 2 is a partially cutaway view of an outer circumferential surface of an example of the compression band 12. As depicted in FIG. 2, the compression band 12 includes a band-shaped outer bag 20 consisting of an outer circumferential side surface nonwoven fabric 20a and an inner circumferential side nonwoven fabric not depicted made of synthetic resin fiber and having rear surfaces laminated with each other by synthetic resin such as PVC, as well as an upstream expansion bag 22, an intermediate expansion bag 24, and a downstream expansion bag 26 that are housed in order in the width direction within the band-shaped outer bag 20, that are made up of flexible sheets such as soft polyvinyl chloride sheets, for example, and that are capable of independently compressing the upper arm 10, and the compression band 12 is removably mounted on the upper arm 10 by causing a raised pile not depicted attached to an end portion of the inner circumferential side nonwoven fabric to removably adhere to a hook-and-loop fastener 28 attached to an end portion of the outer circumferential side surface nonwoven fabric 20a. While being mounted on the upper arm 10, the downstream expansion bag 26 is positioned on a downstream side of the artery 16 in the upper arm 10 relative to the upstream expansion bag 22 and the intermediate expansion bag 24. The intermediate expansion bag 24 is positioned on an upstream side relative to the downstream expansion bag 26, and the upstream expansion bag 22 is positioned on an upstream side relative to the downstream expansion bag 26 and the intermediate expansion bag 24. The upstream expansion bag 22, the intermediate expansion bag 24, and the downstream expansion bag 26 respectively have independent air chambers aligned in the width direction to respectively compress the upper arm 10 and include tube connecting connectors 32, 34, and 36 on an outer circumferential surface side. The tube connecting connectors 32, 34, and 36 are exposed on the outer circumferential surface of the compression band 12 through the outer circumferential side surface nonwoven fabric 20a.

Figure 3:
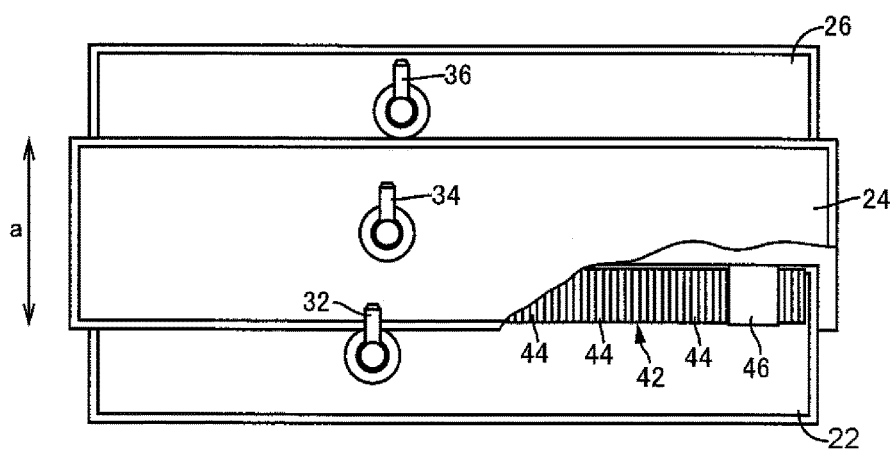
FIG. 3 is a plane view of an upstream expansion bag, an intermediate expansion bag, and a downstream expansion bag included in the compression band of FIG. 2.
Figure 4:
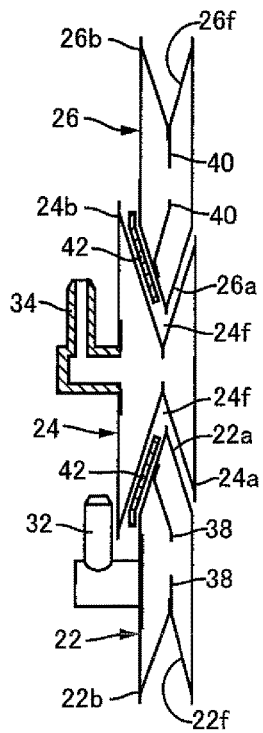
FIG. 4 is a cross-sectional view of the upstream expansion bag, the intermediate expansion bag, and the downstream expansion bag of FIG. 3 taken along a width direction.

FIG. 3 is a plane view of the upstream expansion bag 22, the intermediate expansion bag 24, and the downstream expansion bag 26 included in the compression band 12, and FIG. 4 is a cross-sectional view of the bags taken along a width direction thereof, i.e., the direction of an arrow a of FIG. 3. The upstream expansion bag 22, the intermediate expansion bag 24, and the downstream expansion bag 26 are bags for detecting a pulse wave that is pressure oscillation generated in response to a volume change in the artery 16 compressed by the bags and each has a longitudinal shape. The upstream expansion bag 22 and the downstream expansion bag 26 are arranged to be adjacent to both sides of the intermediate expansion bag 24. The intermediate expansion bag 24 is located at a center portion of the compression band 12 in the width direction to be interposed between the upstream expansion bag 22 and the downstream expansion bag 26. While the compression band 12 is wrapped around the upper arm 10, the upstream expansion bag 22 and the downstream expansion bag 26 are arranged across a predetermined distance in the longitudinal direction of the upper arm 10 and the intermediate expansion bag 24 is located between the upstream expansion bag 22 and the downstream expansion bag 26 to align in the longitudinal direction of the upper arm 10.

The intermediate expansion bag 24 includes side edge portions of a so-called gusset structure on the both sides. In particular, both end portions of the intermediate expansion bag 24 in the longitudinal direction of the upper arm 10 are provided with a pair of respective folded grooves 24f and 24f made up of flexible sheets folded in the direction coming closer to each other such that a depth increases as the sheets come closer to each other. Adjacent side end portions 22a and 26a of the upstream expansion bag 22 and the downstream expansion bag 26 on sides adjacent to the intermediate expansion bag 24 are inserted and disposed in the pair of the folded grooves 24f and 24f. This leads to a mutually overlapping structure, i.e., an overlap structure, of the both end portions of the intermediate expansion bag 24, the adjacent side end portion 22a of the upstream expansion bag 22 and the adjacent side end portion 26a of the downstream expansion bag 26 and, therefore, when the upstream expansion bag 22, the intermediate expansion bag 24, and the downstream expansion bag 26 compress the upper arm 10 at equal pressure, uniform pressure distribution is acquired even near boundaries thereof.

The upstream expansion bag 22 and the downstream expansion bag 26 also include side edge portions of the so-called gusset structure in end portions 22b and 26b on the side opposite to the intermediate expansion bag 24. In particular, the end portions 22b and 26b of the upstream expansion bag 22 and the downstream expansion bag 26 on the side opposite to the intermediate expansion bag 24 are provided with a pair of respective folded grooves 22f and 26f made up of flexible sheets folded in the direction coming closer to each other such that a depth increases as the sheets come closer to each other. The sheets making up the folded grooves 22f and 26f are connected to opposite side portions, i.e., portions on the intermediate expansion bag 24 side, via connection sheets 38, 40 including through-holes disposed in the upstream expansion bag 22 and the downstream expansion bag 26 so as not to jump out in the width direction. As a result, the compression pressure to the artery 16 of the upper arm 10 can be acquired in the end portions 22b and 26b of the upstream expansion bag 22 and the downstream expansion bag 26 as is the case with the other portions and, therefore, an effective compression width of the compression band 12 in the width direction becomes equivalent to a width dimension thereof. The compression band 12 is about 12 cm in the width direction and has a structure with the three bags, i.e., the upstream expansion bag 22, the intermediate expansion bag 24, and the downstream expansion bag 26, arranged in the width direction and, therefore, each of the bags must have a width dimension of substantially about 4 cm. To generate a sufficient compression function even with such a narrow width dimension, an overlap structure is formed by mutually overlapping both end portions 24a and 24b of the intermediate expansion bag 24 and the adjacent side end portions 22a and 26a of the upstream expansion bag 22 and the downstream expansion bag 26, and the end portions 22b and 26b of the upstream expansion bag 22 and the downstream expansion bag 26 on the side opposite to the intermediate expansion bag 24 are formed as the side edge portions of the so-called gusset structure.

Each of longitudinal shield members 42 having rigidity anisotropy making the bending rigidity in the width direction of the compression band 12 higher than the bending rigidity in the longitudinal direction of the compression band 12 is interposed between each of the end portions 22a and 26a of the upstream expansion bag 22 and the downstream expansion bag 26 on the intermediate expansion bag 24 side and an inner wall surface, i.e., an opposed groove side surface, of a pair of the folded grooves 24f and 24f in which the end portions are inserted. The shield members 42 have the same length dimension as the upstream expansion bag 22 and the downstream expansion bag 26 or the intermediate expansion bag 24. In this example, as depicted in FIGS. 3 and 4, the longitudinal shield members 42 are respectively interposed in a gap on an outer circumferential side out of gaps between the end portion 22a of the upstream expansion bag 22 and the folded groove 24f in which the end portion is inserted, and a gap on an outer circumferential side out of gaps between the end portion 26a of the downstream expansion bag 26 and the folded groove 24f in which the end portion is inserted; however, the longitudinal shield members 42 may be interposed in inner circumferential gaps. Since a larger shielding effect is produced by the outer circumferential gaps as compared to the inner circumferential gaps, the shield members 42 may be disposed at least in the outer circumferential gaps.

The shield members 42 is made up of a plurality of flexible hollow tubes 44 made of resin parallel to the longitudinal direction of the upper arm 10, i.e., the width direction of the compression band 12, arranged in parallel with each other to align in the circumferential direction of the upper arm 10, i.e., the longitudinal direction of the compression band 12, such that the flexible hollow tubes 44 are coupled to each other directly by molding or adhesive bonding or indirectly via another member such as a flexible sheet like an adhesive tape. The shield members 42 are hooked by a plurality of hook sheets 46 disposed on a plurality of positions on outer circumferential sides of the end portions 22a and 26a of the upstream expansion bag 22 and the downstream expansion bag 26 on the intermediate expansion bag 24 side.

Returning to FIG. 1, the automatic blood pressure measuring apparatus 14 has an air pump 50, a quick exhaust valve 52, and an exhaust control valve 54 each connected to a main pipe 56. The main pipe 56 is branched into a first branch pipe 58 connected to the upstream expansion bag 22, a second branch pipe 62 connected to the intermediate expansion bag 24, and a third branch pipe 64 connected to the downstream expansion bag 26. The first branch pipe 58 includes a first on-off valve E1 in series for directly opening/closing a section between the air pump 50 and the upstream expansion bag 22. The main pipe 56 includes a second on-off valve E2 in series for directly opening/closing a section from the air pump 50, the quick exhaust valve 52, and the exhaust control valve 54 to the branch pipes. The third branch pipe 64 includes a third on-off valve E3 in series for directly opening/closing a section between the air pump 50 and the downstream expansion bag 26. A first pressure sensor T1 for detecting a pressure value in the upstream expansion bag 22 is connected to the first branch pipe 58; a second pressure sensor T2 for detecting a pressure value in the intermediate expansion bag 24 is connected to the second branch pipe 62; and a third pressure sensor T3 for detecting a pressure value in the downstream expansion bag 26 is connected to the third branch pipe 64.

The first pressure sensor T1, the second pressure sensor T2, and the third pressure sensor T3 supply to an electronic control device 70 an output signal indicative of a pressure value in the upstream expansion bag 22, i.e., a compression pressure value PC1 of the upstream expansion bag 22; an output signal indicative of a pressure value in the intermediate expansion bag 24, i.e., a compression pressure value PC2 of the intermediate expansion bag 24; and an output signal indicative of a pressure value in the downstream expansion bag 26, i.e., a compression pressure value PC3 of the downstream expansion bag 26. The electronic control device 70 is a so-called microcomputer including a CPU 72, a RAM 74, a ROM 76, an I/O port not depicted etc. The electronic control device 70 collects respective pulse wave signals SM1, SM2, and SM3 (see FIGS. 6 to 11 described later) indicative of pulse waves that are pressure oscillations in the expansion bags 22, 24, and 26 respectively generated in response to a volume change in the artery 16 of the upper arm 10 compressed by each of the expansion bags 22, 24, and 26 when the CPU 72 processes input signals in accordance with a program stored in advance in the ROM 76 while utilizing a storage function of the RAM 74 to control each of the electric air pump 50, the quick exhaust valve 52, the exhaust control valve 54, the first on-off valve E1, the second on-off valve E2, and the third on-off valve E3. The electronic control device 70 calculates the maximum blood pressure value SBP and the minimum blood pressure value DBP of the living body based on the pulse wave signals SM1, SM2, and SM3 and displays measurement values that are calculation results on a display device 78. The electronic control device 70 is supplied with an output signal from a blood pressure measurement start sensor 80 in addition to the output signals from the first pressure sensor T1, the second pressure sensor T2, and the third pressure sensor T3. The blood pressure measurement start sensor 80 is a sensor outputting a signal used as a sign for staring blood pressure measurement and outputs the signal when a start-up operation device not depicted is operated, for example.

Figure 5:
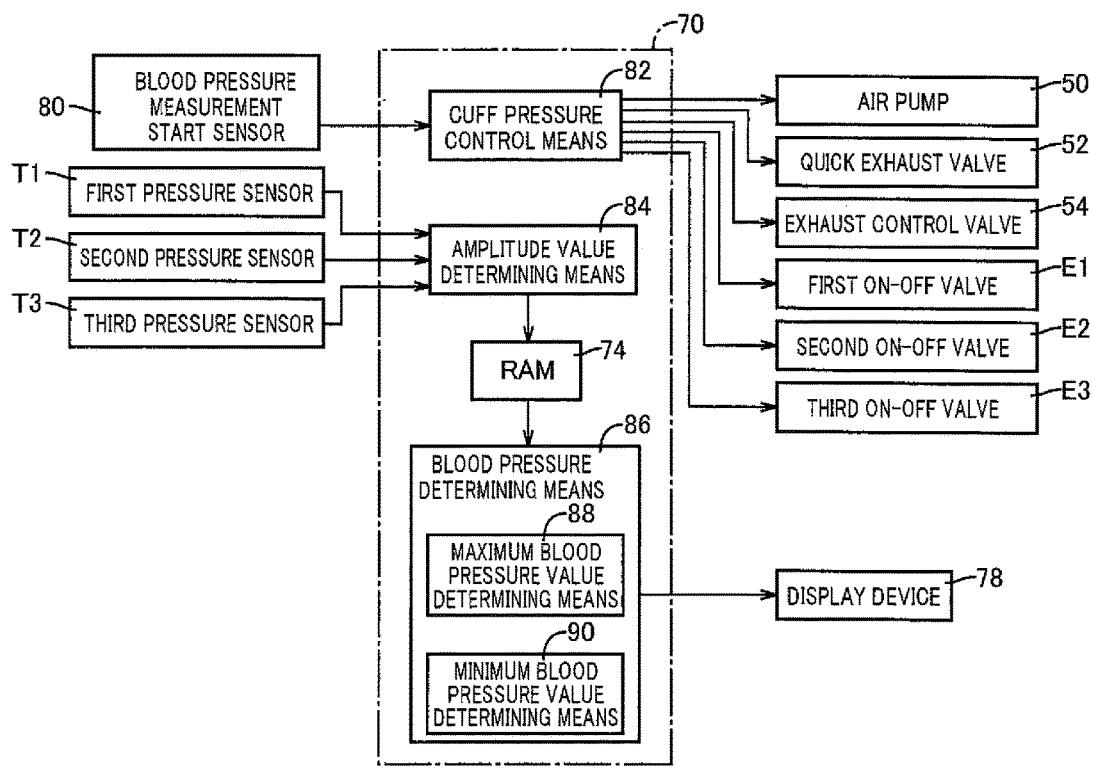
FIG. 5 is a functional block diagram for explaining a main portion of the control function included in an electronic control device of FIG. 1.
Figure 6:
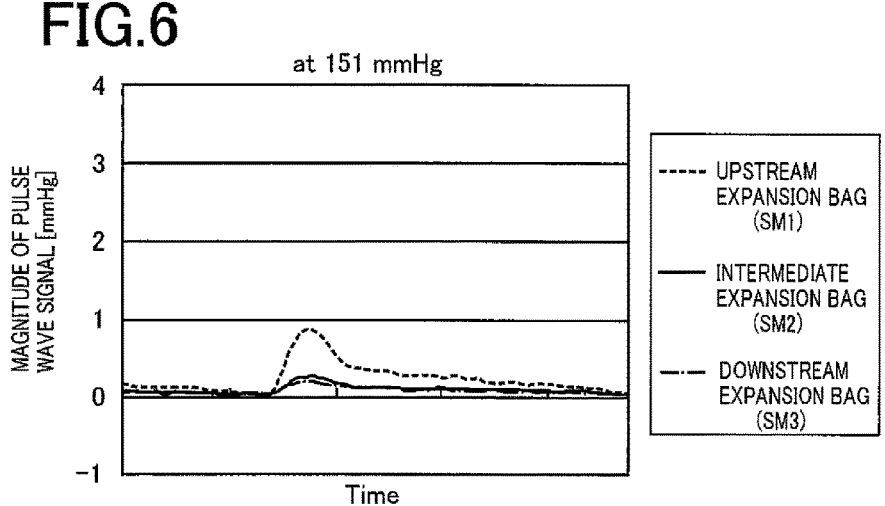
FIG. 6 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 151 mmHg.
Figure 7:
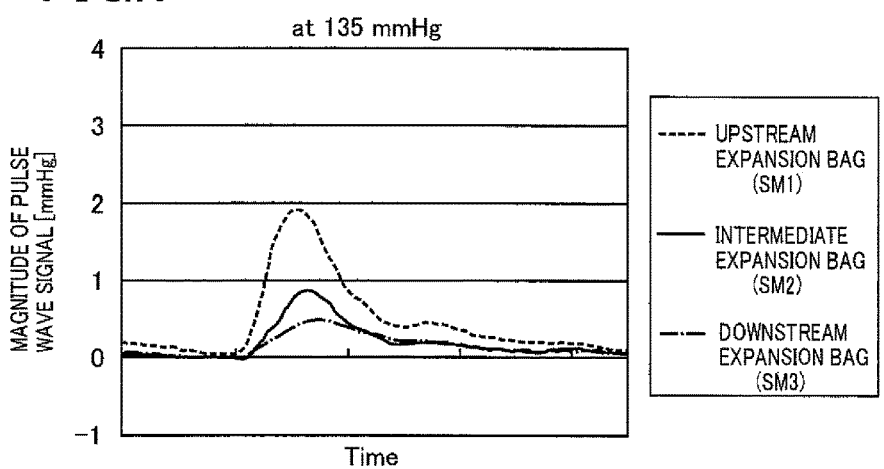
FIG. 7 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 135 mmHg.
Figure 8:
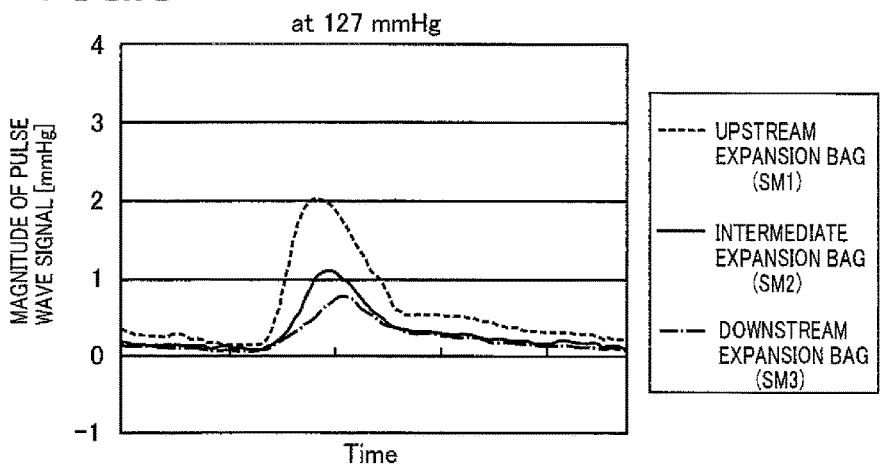
FIG. 8 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 127 mmHg.
Figure 9:
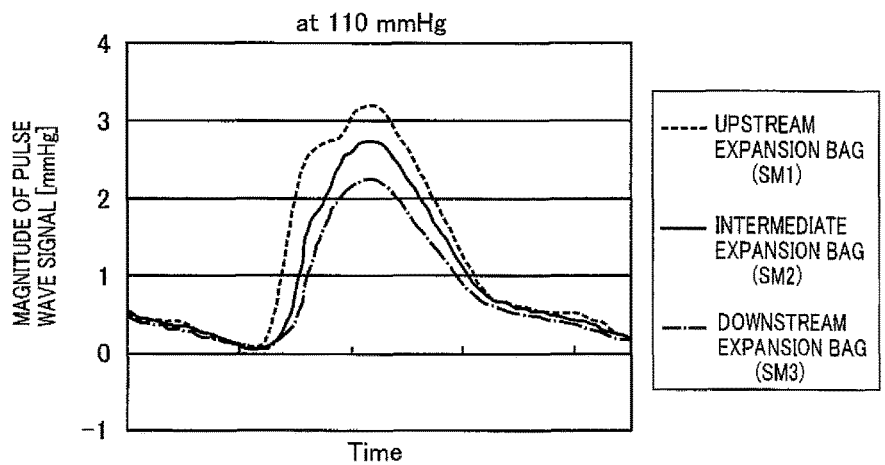
FIG. 9 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 110 mmHg.
Figure 10:
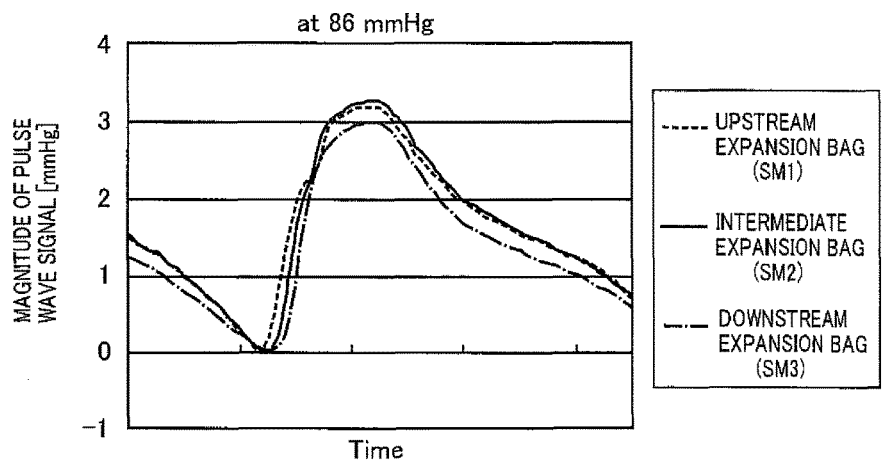
FIG. 10 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 86 mmHg.
Figure 11:
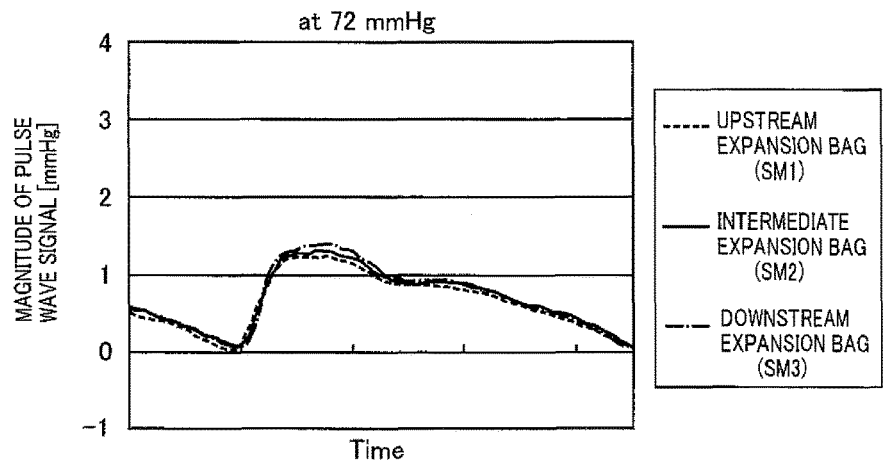
FIG. 11 is a diagram of pulse wave signals from a plurality of the expansion bags generated in a process of gradual reduction of each of compression pressure values of the plurality of the expansion bags by a cuff pressure control means of FIG. 5 and it is a diagram when the compression pressure value is 72 mmHg.

FIG. 5 is a functional block diagram for explaining a main portion of the control function included in the electronic control device 70. In FIG. 5, if the signal used as a sign for staring the blood pressure measurement is supplied from the blood pressure measurement start sensor 80, a cuff pressure control means 82 controls each of the electric air pump 50, the quick exhaust valve 52, the exhaust control valve 54, the first on-off valve E1, the second on-off valve E2, and the third on-off valve E3 to rapidly increase the compression pressure values PC of the expansion bags 22, 24, and 26 for the artery 16 of the upper arm 10 at the same time to a pressurization target pressure value PCM (e.g., 180 mmHg) preset to a value sufficiently higher than the maximum blood pressure value SBP in the artery 16. For example, the expansion bags are pressurized until the compression pressure value PC2 of the intermediate expansion bag 24 becomes equal to or greater than the pressurization target pressure value PCM. Subsequently, the cuff pressure control means 82 gradually reduces the compression pressure values PC of the pressurized expansion bags 22, 24, and 26 at the same time continuously or in stages at a gradual pressure reduction speed preset to about 3 to 5 mmHg/sec, for example. On this occasion, the cuff pressure control means 82 retains each of the compression pressure values PC of the expansion bags 22, 24, and 26 for a predetermined time each time a predetermined amount (e.g., within a range of 1 to 10 mmHg) of pressure is gradually reduced. When the compression pressure value PC2 of the intermediate expansion bag 24 becomes smaller than a measurement termination pressure value PCE (e.g., 30 mmHg) preset to a value sufficiently lower than the minimum blood pressure value DBP in the artery 16, the cuff pressure control means 82 discharges the pressures in the expansion bags 22, 24, and 26 to an atmospheric pressure by using the quick exhaust valve 52.

An amplitude value determining means 84 sequentially collects the pulse wave signals SM1, SM2, and SM3 indicative of pulse waves that are mutually synchronized pressure variations in the expansion bags 22, 24, and 26 in sampling periods sufficiently shorter than a pulse period, for example, in periods of a few milliseconds to a few tens of milliseconds, based on the output signals from the first pressure sensor T1, the second pressure sensor T2, and the third pressure sensor T3 in the process of the gradual reduction of each of the compression pressure values PC of the expansion bags 22, 24, and 26 by the cuff pressure control means 82. FIGS. 6 to 11 are diagrams of exemplary illustration of the pulse wave signals SM generated in the process with curves connecting time discrete data points read in the sampling periods. The pulse wave signals SM1, SM2, and SM3 described in FIGS. 6 to 11 are a first pulse wave signal SM1 (broken line) indicative of the pulse wave from the upstream expansion bag 22 acquired by discriminating the output signal from the first pressure sensor T1 through low-pass filter processing or band-pass filter processing; a second pulse wave signal SM2 (solid line) indicative of the pulse wave from the intermediate expansion bag 24 acquired by discriminating the output signal from the second pressure sensor T2 through low-pass filter processing or band-pass filter processing; and a third pulse wave signal SM3 (dashed-dotted line) indicative of the pulse wave from the downstream expansion bag 26 acquired by discriminating the output signal from the third pressure sensor T3 through low-pass filter processing or band-pass filter processing, when the compression pressure value PC of the compression band 12 is 151 mmHg, 135 mmHg, 127 mmHg, 110 mmHg, 86 mmHg, and 72 mmHg, for example. The amplitude value determining means 84 sequentially determines amplitude values A1, A2, and A3 of the mutually synchronized pulse wave signals SM1, SM2, and SM3 within one pulse wave in sampling periods sufficiently shorter than a pulse period, for example, in periods of a few milliseconds to a few tens of milliseconds and stores the amplitude values A1 to A3 in a predetermined storage area in the RAM 74 along with a cuff pressure signal PK2 indicative of the compression pressure value PC2 of the intermediate expansion bag 24 corresponding to the pulse wave signals SM from which the amplitude values A1, A2, and A3 are determined.

With regard to a pair of pulse waves out of the first pulse wave signal SM1, the second pulse wave signal SM2, and the third pulse wave signal SM3 acquired in the reduction process of the compression pressure of the compression band 12, since a downstream pulse wave is smaller and generated later than an upstream pulse wave, an amplitude ratio of the downstream pulse wave to the upstream pulse wave has a property that, although indicating a relatively constant value before the maximum blood pressure value SBP, the ratio relatively abruptly increases when the maximum blood pressure value SBP is nearly reached, for example, in an area after an inflection point b1 of the first pulse wave signal SM1, and a blood pressure value determining means 86 includes a maximum blood pressure value determining means 88 utilizing this property to determine the maximum blood pressure value SBP of the living body based on the compression pressure when the abrupt increase is judged. For example, the maximum blood pressure value determining means 88 sequentially calculates each of a first amplitude ratio R21 that is a ratio (A2/A1) of the amplitude A2 of the pulse wave signal SM2 from the intermediate expansion bag 24 to the amplitude A1 of the pulse wave signal SM1 from the upstream expansion bag 22, a second amplitude ratio R32 that is a ratio (A3/A2) of the amplitude A3 of the pulse wave signal SM3 from the downstream expansion bag 26 to the amplitude A2 of the pulse wave signal SM2 from the intermediate expansion bag 24, and a third amplitude ratio R31 that is a ratio (A3/A1) of the amplitude A3 of the pulse wave signal SM3 from the downstream expansion bag 26 to the amplitude A1 of the pulse wave signal SM1 from the upstream expansion bag 22, within one pulse wave, for example, in the sampling periods, from the amplitude values A1, A2, and A3 of the first, second and third pulse wave signals SM1, SM2, and SM3 sequentially determined by the amplitude value determining means 84 in the sampling periods sufficiently shorter than one pulse period. Subsequently, the maximum blood pressure value determining means 88 judges that the first amplitude ratio R21 exceeds a preset first amplitude ratio change judgment value RR1 and/or that the second amplitude ratio R32 exceeds a preset second amplitude ratio change judgment value RR2, and determines the maximum blood pressure value SBP based on the compression pressure value PC2 of the intermediate expansion bag 24 when the judgment becomes affirmative. Alternatively, the maximum blood pressure value determining means 88 judges that the third amplitude ratio R31 exceeds a preset third amplitude ratio change judgment value RR3, and determines the maximum blood pressure value SBP based on the compression pressure value PC2 of the intermediate expansion bag 24 when the judgment becomes affirmative. Alternatively, the maximum blood pressure value determining means 88 judges that the first amplitude ratio R21 exceeds the preset first amplitude ratio change judgment value RR1, and determines the maximum blood pressure value SBP based on the compression pressure value PC2 of the intermediate expansion bag 24 when the judgment becomes affirmative.

The maximum blood pressure value determining means 88 may directly determine as the maximum blood pressure value SBP the compression pressure value PC2 of the intermediate expansion bag 24 when the judgment becomes affirmative, or may determine as the maximum blood pressure value SBP a value after correction of the compression pressure value PC2 for matching with a measurement value of a mercurial sphygmomanometer. When the maximum blood pressure value SBP is determined, it is desirable to use the judgment based on a change in the second amplitude ratio R32 or the third amplitude ratio R31 reflecting a restart of a blood flow immediately beneath the downstream expansion bag 26; however, the judgment based on a change in the first amplitude ratio R21 reflecting a restart of a blood flow immediately beneath the intermediate expansion bag 24 may also be used. In this case, the maximum blood pressure value SBP can be determined by correction with a preset correction value from the compression pressure value PC2 of the intermediate expansion bag 24 when it is determined that the first amplitude ratio R21 exceeds the preset first amplitude ratio change judgment value RR1.

Figure 12:
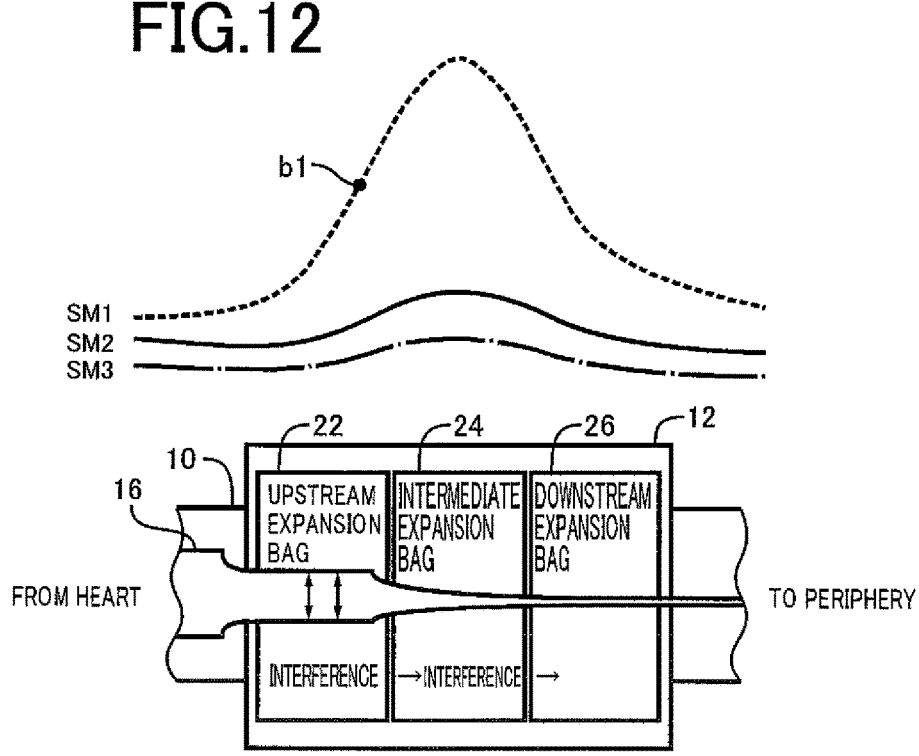
FIG. 12 is a diagram for explaining shapes of a first pulse wave signal from the upstream expansion bag of a cuff band, a second pulse wave signal from the intermediate expansion bag, and a third pulse wave signal from the downstream expansion bag at a compression pressure higher than a maximum blood pressure value in comparison with compression states of an artery immediately beneath the upstream expansion bag, the intermediate expansion bag, and the downstream expansion bag.
Figure 13:
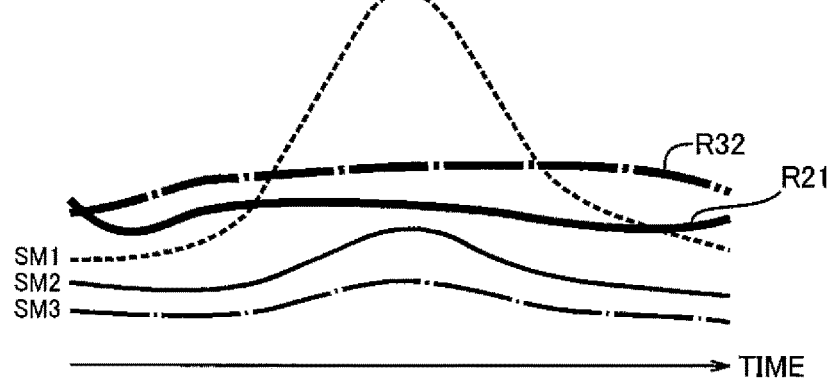
FIG. 13 is a diagram for explaining shapes of a first pulse wave signal from the upstream expansion bag of a cuff band, a second pulse wave signal from the intermediate expansion bag, and a third pulse wave signal from the downstream expansion bag at a compression pressure lower than a maximum blood pressure value in comparison with compression states of an artery immediately beneath the upstream expansion bag, the intermediate expansion bag, and the downstream expansion bag.

The first amplitude ratio change judgment value RR1, the second amplitude ratio change judgment value RR2, and the third amplitude ratio change judgment value RR3 are empirically defined in advance for judging a rise of the first amplitude ratio R21, the second amplitude ratio R32, and the third amplitude ratio R31 at the restart of the blood flow. Crosstalk exists among the upstream expansion bag 22, the intermediate expansion bag 24, and the downstream expansion bag 26 and, in the stage before the start of the blood flow, as depicted in FIG. 12, the first pulse wave signal SM1 of the upstream expansion bag 22 is transmitted to the intermediate expansion bag 24 at a constant transmission rate of about 0.3 to generate the second pulse wave signal SM2 while the second pulse wave signal SM2 of the intermediate expansion bag 24 is transmitted to the downstream expansion bag 26 at a constant transmission rate of about 0.3 to generate the third pulse wave signal SM3. Therefore, with regard to the first amplitude ratio R21 that is a ratio (A2/A1) of the amplitude A2 of the pulse wave signal SM2 from the intermediate expansion bag 24 to the amplitude A1 of the pulse wave signal SM1 from the upstream expansion bag 22, the second amplitude ratio R32 that is a ratio (A3/A2) of the amplitude A3 of the pulse wave signal SM3 from the downstream expansion bag 26 to the amplitude A2 of the pulse wave signal SM2 from the intermediate expansion bag 24, and the third amplitude ratio R31 that is a ratio (A3/A1) of the amplitude A3 of the pulse wave signal SM3 from the downstream expansion bag 26 to the amplitude A1 of the pulse wave signal SM1 from the upstream expansion bag 22, the amplitude ratios are substantially constant within one pulse as depicted in FIG. 13.

Figure 14:
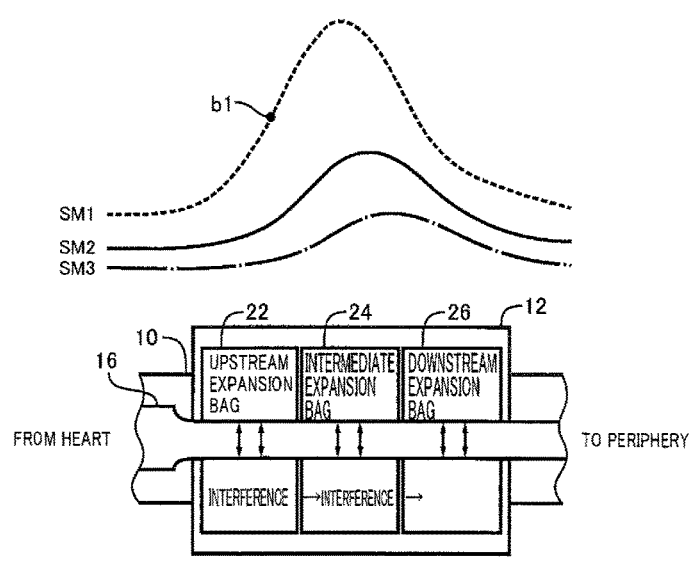
FIG. 14 is a diagram of the shapes of the first pulse wave signal, the second pulse wave signal, and third pulse wave signal, and a first amplitude ratio and a second amplitude ratio obtained from the signals, while the compression pressure is higher than the maximum blood pressure value of the living body.
Figure 15:
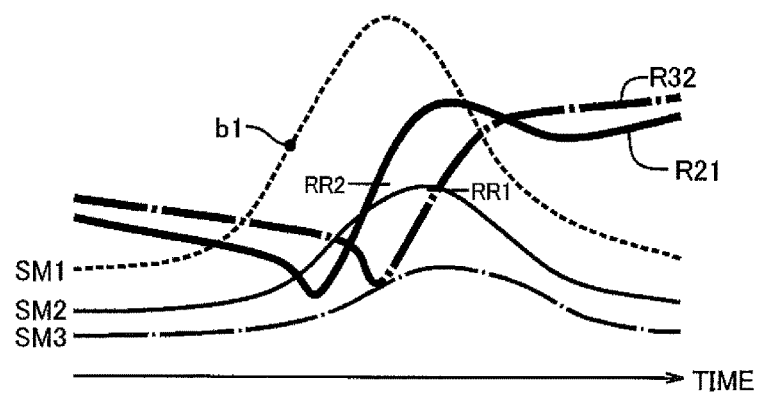
FIG. 15 is a diagram of the shapes of the first pulse wave signal, the second pulse wave signal, and third pulse wave signal, and a first amplitude ratio and a second amplitude ratio obtained from the signals, while the compression pressure is lower than the maximum blood pressure value of the living body.

However, at the start of the blood flow, as depicted in FIG. 14, the second pulse wave signal SM2 and the third pulse wave signal SM3 are influenced by a vascular volume change at the start of the blood flow in addition to the crosstalk and indicate a pulse wave larger as compared to before the start of the blood flow with a peak thereof generated with a delay. Therefore, the first amplitude ratio R21 and the second amplitude ratio R32 as well as the third amplitude ratio R31 (same as the first amplitude ratio R21 and the second amplitude ratio R32 although not depicted) abruptly rise within one pulse after the inflection point b1 of the first pulse wave signal SM1 as depicted in FIG. 15. To judge the rising, the first amplitude ratio change judgment value RR1, the second amplitude ratio change judgment value RR2, and the third amplitude ratio change judgment value RR3 are set to values larger than variations of the first amplitude ratio R21 and the second amplitude ratio R32 as well as the third amplitude ratio R31 before the start of the blood flow and before the inflection point b1 and smaller than rising widths of the first amplitude ratio R21 and the second amplitude ratio R32 as well as the third amplitude ratio R31 at the start of the blood flow.

Figure 16:
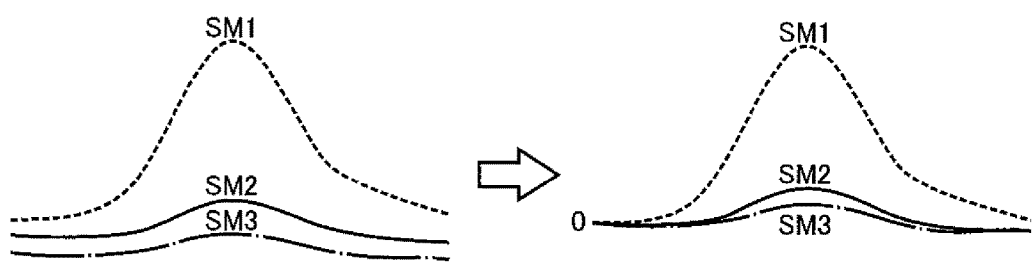
FIG. 16 is a diagram for explaining preprocessing executed to conform start points of wave pulse signals when amplitude values of the first pulse wave signal, the second pulse wave signal and the third pulse wave signal are calculated from the first pulse wave signal, the second pulse wave signal and the third pulse wave signal.

Preferably, if preprocessing is executed to conform the values of start (leftmost) points of the second pulse wave signal SM2 and the third pulse wave signal SM3 to the value of a start (leftmost) point of the first pulse wave signal SM1 before calculation of the first amplitude ratio R21 and the second amplitude ratio R32 as well as the third amplitude ratio R31, the initial values of the pulse wave signals can be set to a common zero value to facilitate the calculation of the amplitudes A1, A2, and A3 as depicted from the left side to the right side of FIG. 16 and, thus, the first amplitude ratio R21 and the second amplitude ratio R32 as well as the third amplitude ratio R31 are easily calculated.

Figure 17:
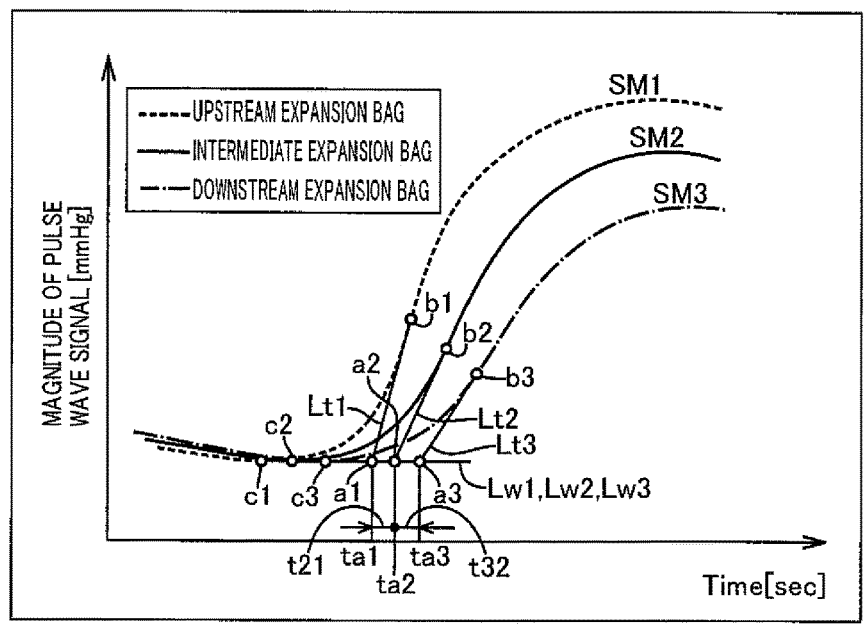
FIG. 17 is a diagram of rising points of the pulse wave signals from the plurality of the expansion bags indicated in two-dimensional coordinates of a time axis and a compression pressure value axis, and time differences between the rising points.

The blood pressure value determining means 86 includes a minimum blood pressure value determining means 90 determining the minimum blood pressure value DBP of the living body based on a phase difference between pulse wave signals from at least two of the multiple expansion bags 22, 24, and 26 and a pulse wave propagation speed PWV [m/sec] in the artery 16 under compression by the compression band 12. Specifically, in the process of gradual reduction of each of the compression pressure values PC of the pressurized expansion bags 22, 24, and 26 while the upper arm 10 is compressed by the expansion bags 22, 24, and 26 at the same respective pressures, the minimum blood pressure value determining means 90 sequentially calculates each of a first time difference t32 between a rising point a3 of the pulse wave signal SM3 from the downstream expansion bag 26 and a rising point a2 of the pulse wave signal SM2 from the intermediate expansion bag 24 indicated in two-dimensional coordinates of a time axis and a compression pressure value axis as depicted in FIG. 17, for example; a second time difference t21 between the rising point a2 of the pulse wave signal SM2 from the intermediate expansion bag 24 and a rising point a1 of the pulse wave signal SM1 from the upstream expansion bag 22 indicated in the two-dimensional coordinates; and a third time difference t31 between the rising point a3 of the pulse wave signal SM3 from the downstream expansion bag 26 and the rising point a1 of the pulse wave signal SM1 from the upstream expansion bag 22. The first time difference t32, the second time difference t21, and the third time difference t31 correspond to the phase difference.

In this example, the rising point a1 is an intersection between a tangent Lt1 at the inflection point b1 of a rising portion of the pulse wave signal SM1 and a horizontal line Lw1 parallel to the time axis passing through a rising start point c1 of the pulse wave signal SM1. The rising point a2 is an intersection between a tangent Lt2 at an inflection point b2 of a rising portion of the pulse wave signal SM2 and a horizontal line Lw2 parallel to the time axis passing through a rising start point c2 of the pulse wave signal SM2. The rising point a3 is an intersection between a tangent Lt3 at an inflection point b3 of a rising portion of the pulse wave signal SM3 and a horizontal line Lw3 parallel to the time axis passing through a rising start point c3 of the pulse wave signal SM3.

In the process of gradual reduction of each of the compression pressure values PC of the pressurized expansion bags 22, 24, and 26 while the upper arm 10 is compressed by the expansion bags 22, 24, and 26 at the same respective pressures, the minimum blood pressure value determining means 90 sequentially calculates the pulse wave propagation speed PWV in the artery 16 under compression by the compression band 12 and sequentially calculates a change rate $R_{PWV}$ of the pulse wave propagation speed PWV to the compression pressure value PC2 of the intermediate expansion bag 24. For example, the pulse wave propagation speed PWV is calculated by dividing the calculated first time difference t32 or the second time difference t21 by a distance L32 (see FIG. 4) in the width direction between the intermediate expansion bag 24 and the downstream expansion bag 26, by a distance L21 (see FIG. 4) in the width direction between the upstream expansion bag 22 and the intermediate expansion bag 24, or by a distance (L21+L32) in the width direction between the upstream expansion bag 22 and the downstream expansion bag 26. For example, the change rate $R_{PWV}$ of the pulse wave propagation speed PWV is represented by a slope of a tangent of a curve representative of a relationship between the pulse wave propagation speed PWV and the compression pressure value PC2 indicated in two-dimensional coordinates of a compression pressure value axis and a pulse wave propagation speed axis as depicted in FIG. 18.

Figure 18:
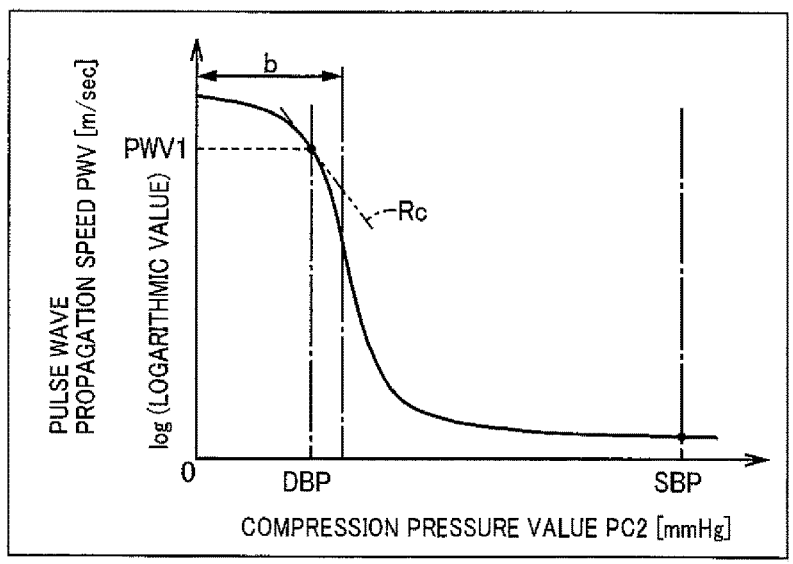
FIG. 18 is a diagram of relationship between a pulse wave propagation speed in the artery under compression by the compression band and a compression pressure value.

In the process of gradual reduction of each of the compression pressure values PC of the pressurized expansion bags 22, 24, and 26 while the upper arm 10 is compressed by the expansion bags 22, 24, and 26 at the same respective pressures, the minimum blood pressure value determining means 90 determines as the minimum blood pressure value DBP of the living body the compression pressure value PC2, for example, when the first time difference t32 passes through a preset time difference judgment value tc, i.e., is smaller than the time difference judgment value tc; the second time difference 121 passes through the time difference judgment value tc, i.e., is smaller than the time difference judgment value tc; or the third time difference t31 is smaller than the time difference judgment value tc×2, and when the change rate $R_{PWV}$ of the pulse wave propagation speed PWV passes through a preset change rate judgment value Rc, i.e., is smaller than the change rate judgment value Rc, in an area b in which the change rate $R_{PWV}$ continuously increases as the compression pressure value PC2 increases from a lower limit value, for example, zero, as depicted in FIG. 18.

FIG. 18 is a diagram of relationship between a logarithmic value log PWV of the pulse wave propagation speed PWV [m/sec] in the artery 16 under compression by the compression band 12 and the compression pressure value PC2 [mmHg]. As depicted in FIG. 18, as the compression pressure value PC2 increases from zero, the logarithmic value log PWV of the pulse wave propagation speed PWV moderately decreases in a continuous manner from zero to near the minimum blood pressure value DBP, abruptly decreases in a continuous manner near the point of exceeding the minimum blood pressure value DBP, and then moderately decreases in a continuous manner toward the maximum blood pressure value SBP. Therefore, the pulse wave propagation speed PWV becomes slower when the compression pressure value PC2 becomes larger. In an area indicated by an arrow b in FIG. 18, the change rate $R_{PWV}$ (the slope of the curve) of the logarithmic value log PWV of the pulse wave propagation speed PWV continuously increases as the compression pressure value PC2 increases from zero. Although a pulse wave propagation speed PWV1 differs depending on a measured subject when the compression pressure value PC2 matches the minimum blood pressure value DBP, the change rate $R_{PWV}$ of the pulse wave propagation speed PWV, i.e., the change rate judgment value Rc, is the same value regardless of a measured subject when the compression pressure value PC2 matches the minimum blood pressure value DBP. The change rate judgment value Rc is determined from a preliminarily empirically obtained relationship as depicted in FIG. 18.

Figure 19:
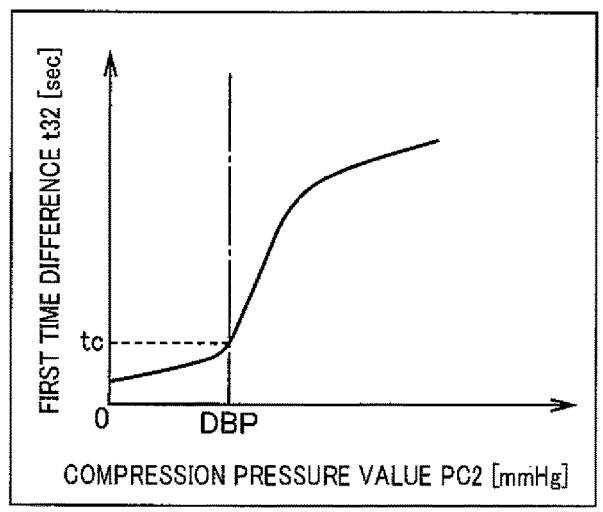
FIG. 19 is a diagram of relationship between a time difference between the third pulse wave signal from the downstream expansion bag and the second pulse wave signal from the intermediate expansion bag, i.e., the first time difference and pressure of the intermediate expansion bag, i.e., the compression pressure value.

FIG. 19 is a diagram of relationship between a time difference between the pulse wave signals from the downstream expansion bag 26 and the intermediate expansion bag 24, i.e., the first time difference t32, and the compression pressure value PC2. As depicted in FIG. 19, the first time difference t32 corresponding to a pulse wave propagation time between the downstream expansion bag 26 and the intermediate expansion bag 24 is the time difference judgment value tc when the compression pressure value PC2 is the minimum blood pressure value DBP. The time difference judgment value tc is determined from a preliminarily empirically obtained relationship as depicted in FIG. 19.

Figure 20:
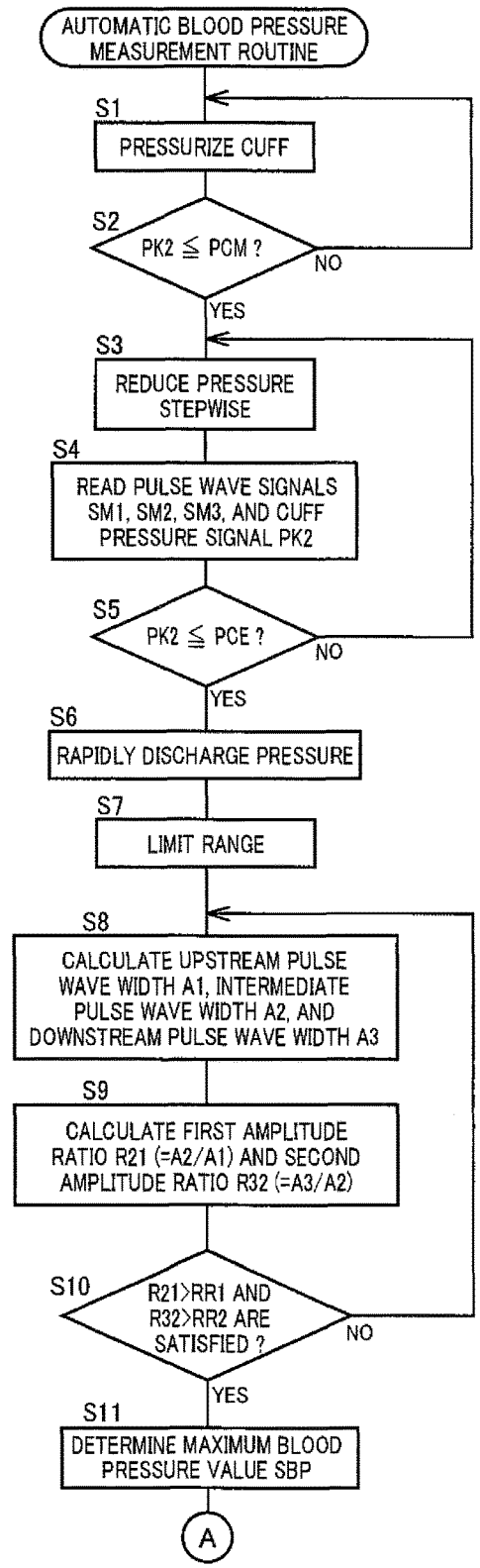
FIG. 20 is one of flowcharts for explaining a main portion of the control operation of the electronic control device of FIG. 5.
Figure 21:
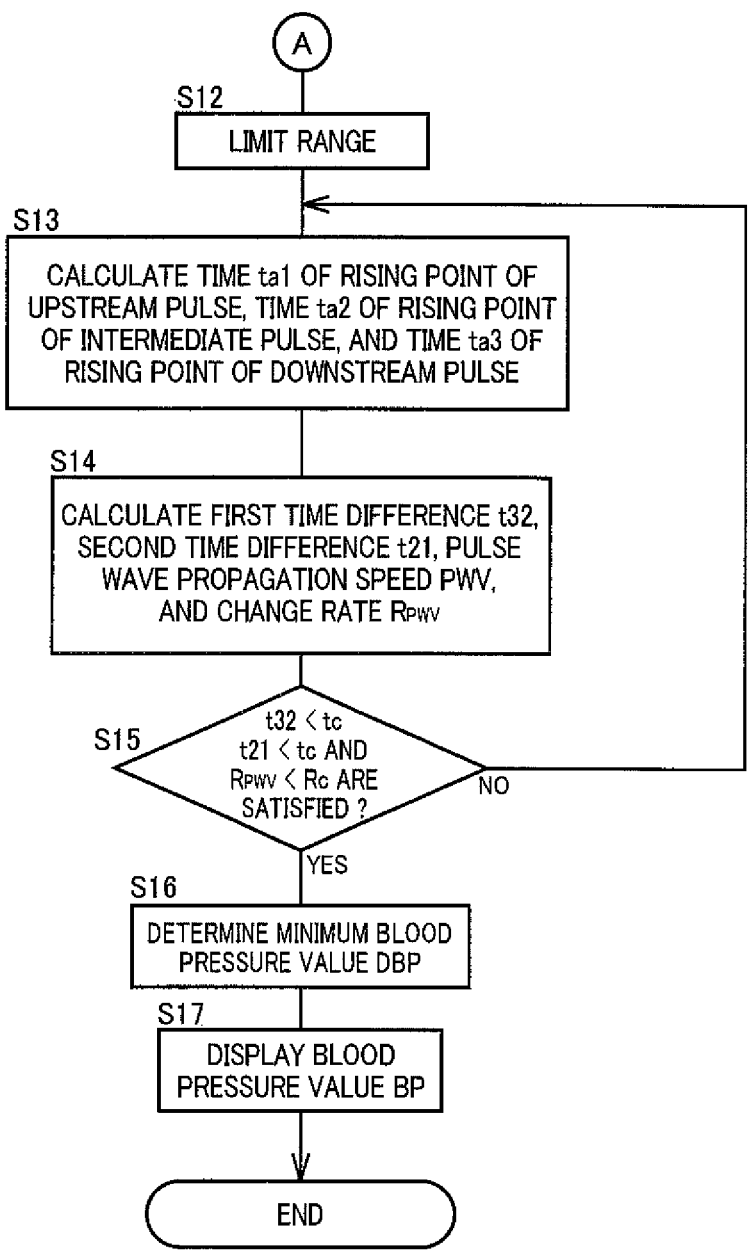
FIG. 21 is the other of flowcharts for explaining a main portion of the control operation of the electronic control device of FIG. 5.
Figure 22:
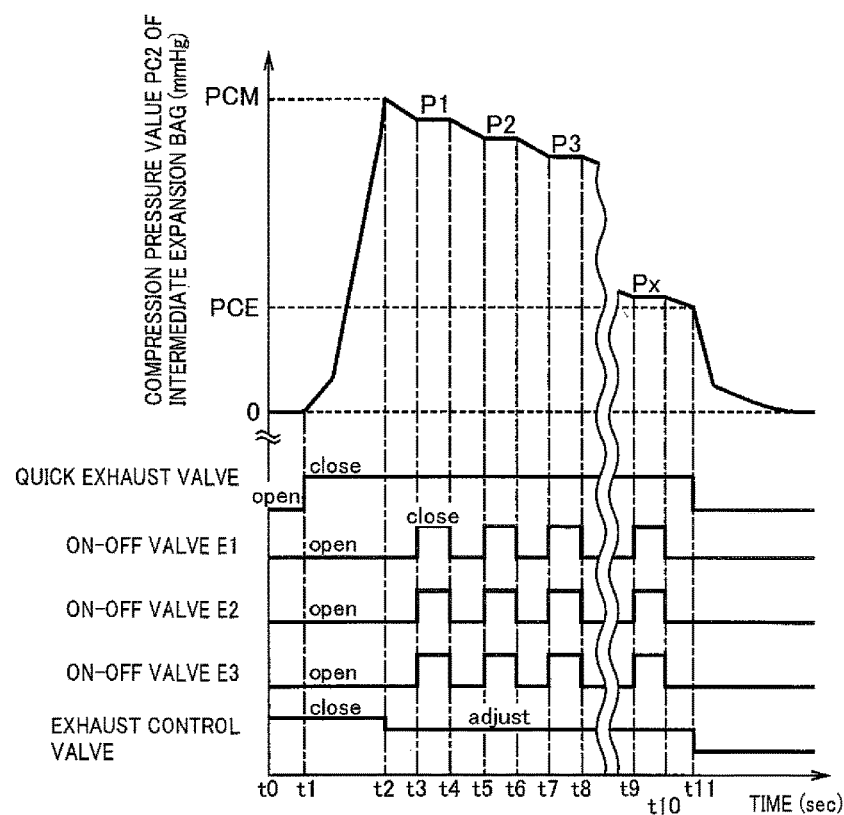
FIG. 22 is a time chart for explaining a main portion of the control operation of the electronic control device of FIG. 5.

FIGS. 20, 21, and 22 are flowcharts and a time chart for explaining a main portion of the control operation of the electronic control device 70. When a power switch not depicted is turned on, an initial state indicated at time t0 of FIG. 22 is achieved. In this state, the first on-off valve E1, the second on-off valve E2, the third on-off valve E3 and the quick exhaust valve 52 are normally opened valves and therefore put into an opened state (non-operating state); the exhaust control valve 54 is a normally closed valve and therefore put into a closed state (non-operating state); and the air pump 50 is put into a non-operating state.

When the start-up operation device not depicted is operated to start the measurement operation of the automatic blood pressure measuring apparatus 14, first, at step (hereinafter, "step" will be omitted) S1 of FIG. 20 corresponding to the cuff pressure control means 82, the compression pressure value of the compression band 12 is increased. Specifically, as depicted in FIG. 22, the quick exhaust valve 52 is put into the closed state while the air pump 50 is put into the operating state to rapidly increase the pressures in the main pipe 56 and the expansion bags 22, 24, and 26 communicating therewith by compressed air sent from the air pump 50. The compression of the upper arm 10 by the compression band 12 is started.

After S1, at S2 corresponding to the cuff pressure control means 82, it is determined whether the compression pressure value PC2 is equal to or greater than the preset pressurization target pressure value PCM (e.g., 180 mmHg), based on the cuff pressure signal PK2 indicative of the compression pressure value PC2 of the intermediate expansion bag 24. At a time point before time t1 of FIG. 22, the determination of S2 is negative and S1 and later of FIG. 20 are repeatedly executed. However, at time t1 of FIG. 22, the determination of S2 becomes affirmative.

If the determination of S2 becomes affirmative as described above, at S3 corresponding to the cuff pressure control means 82, the operation of the air pump 50 is stopped. The exhaust control valve 54 is operated such that the compression pressure values PC1, PC2, and PC3 of the pressurized expansion bags 22, 24, and 26 are concurrently reduced at a gradual pressure reduction speed set in advance to, for example, 3 to 5 mmHg/sec, to start gradual exhaust. The exhaust control valve 54 is controlled such that a reduction amount of the compression pressure values PC of the expansion bags 22, 24, and 26 is a predetermined amount within a range of 1 to 10 mmHg, for example, and the first on-off valve E1, the second on-off valve E2, and the third on-off valve E3 are operated such that each of the compression pressure values PC is retained for a predetermined time each time the predetermined amount is gradually reduced. When the compression pressure values PC are retained, each of the first on-off valve E1, the second on-off valve E2, and the third on-off valve E3 is put into the closed state. Time t2 of FIG. 22 is a start time point of the gradual exhaust, and time t2 to t3 is a time when each of the compression pressure values PC is retained for a predetermined time.

After S3, at S4 corresponding to the amplitude value determining means 84, while each of the compression pressure values PC1, PC2, and PC3 is retained for a predetermined time, the low-pass filter processing or the band-pass filter processing discriminating a signal in a waveband of a few Hz to a few tens of Hz is executed for each of the output signals from the first pressure sensor T1, the second pressure sensor T2, and the third pressure sensor T3 to extract and store the first pulse wave signal SM1, the second pulse wave signal SM2, and the third pulse wave signal SM3 indicative of the pulse waves from the expansion bags 22, 24, and 26, and the low-pass filter processing is executed for the output signal from the second pressure sensor T2 to extract the cuff pressure signal PK2 indicative of the compression pressure value PC2 of the intermediate expansion bag 24 with an AC component removed. The signals are stored in a mutually correlated manner. For example, FIGS. 6 to 11 are diagrams of exemplary illustration of the first pulse wave signal SM1, the second pulse wave signal SM2, and the third pulse wave signal SM3 extracted and stored as described above.

At S4, the first pulse wave signal SM1, the second pulse wave signal SM2, and the third pulse wave signal SM3 are stored along with the cuff pressure signal PK2 corresponding thereto.

After S4, at S5 corresponding to the cuff pressure control means 82, while each of the compression pressure values PC is retained for a predetermined time, it is determined whether the compression pressure value PC2 is equal to or less than the preset measurement termination pressure value PCE (e.g., 30 mmHg) based on the cuff pressure signal PK2 indicative of the compression pressure value PC2 of the intermediate expansion bag 24. At a time point before time t11 of FIG. 22, the determination of S5 is negative and S3 and later of FIG. 20 are repeatedly executed. However, at time t11 of FIG. 22, the determination of S5 becomes affirmative.

If the determination of S5 becomes affirmative as described above, at S6 corresponding to the cuff pressure control means 82, the quick exhaust valve 52 is operated such that each of the pressures of the upstream expansion bag 22, the intermediate expansion bag 24, and the downstream expansion bag 26 is discharged to an atmospheric pressure. Time t11 and later of FIG. 22 indicate this state.

Figure 23:
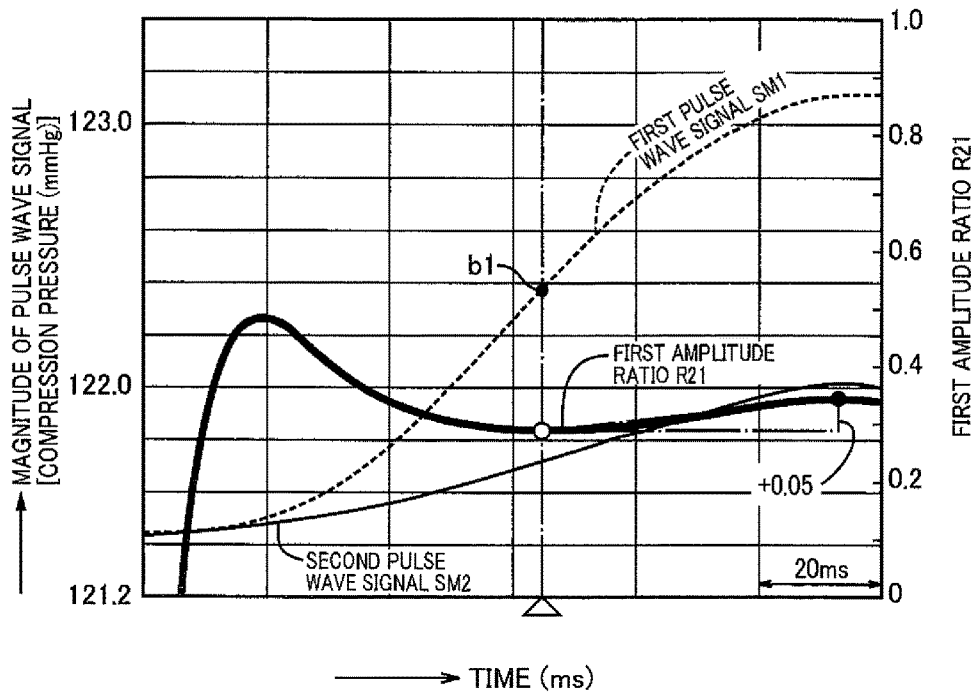
FIG. 23 is a diagram depicted on a time axis of the first pulse wave signal and the second pulse wave signal that is an example before the compression pressure of the compression band reaches the maximum blood pressure value, and the first amplitude ratio calculated from the signals.
Figure 24:
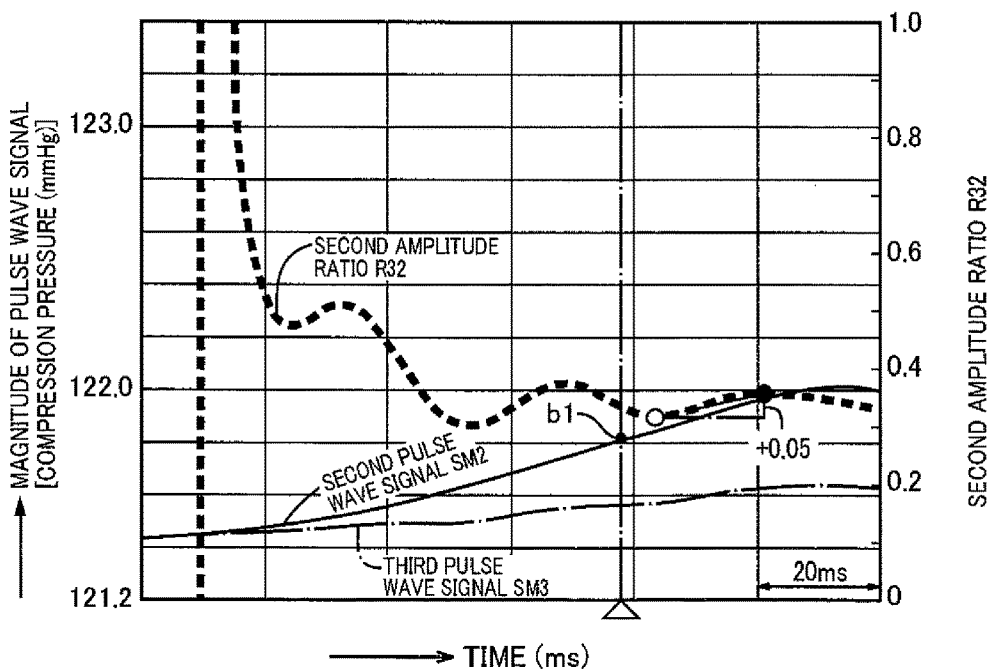
FIG. 24 is a diagram depicted on a time axis of the second pulse wave signal and the third pulse wave signal that is an example before the compression pressure of the compression band reaches the maximum blood pressure value, and the second amplitude ratio calculated from the signals.
Figure 25:
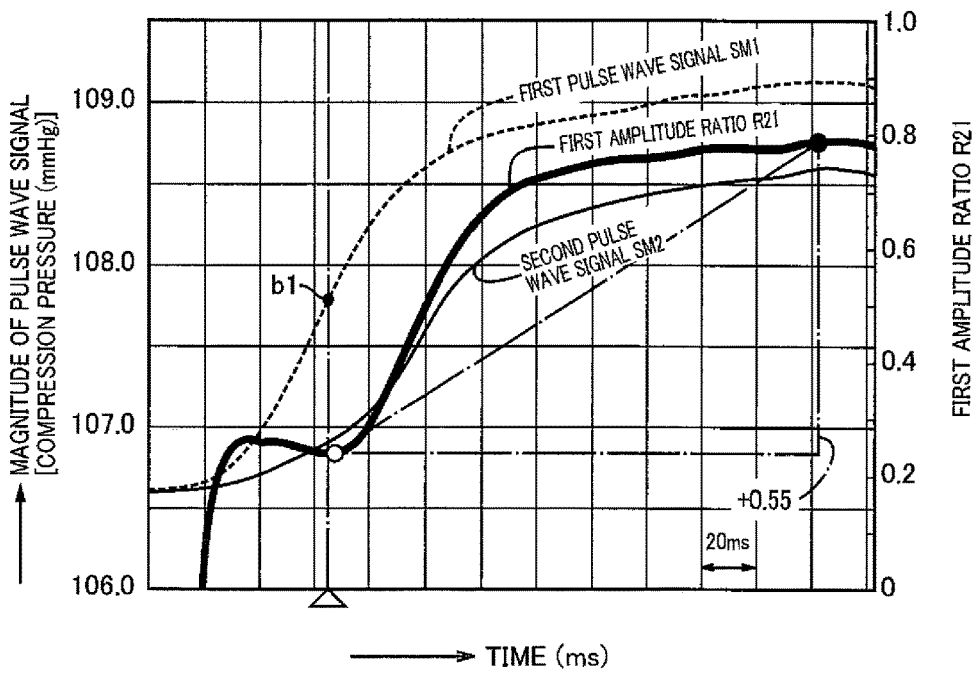
FIG. 25 is a diagram depicted on a time axis of the first pulse wave signal and the second pulse wave signal that is an example when the compression pressure of the compression band reaches the maximum blood pressure value, and the first amplitude ratio calculated from the signals.
Figure 26:
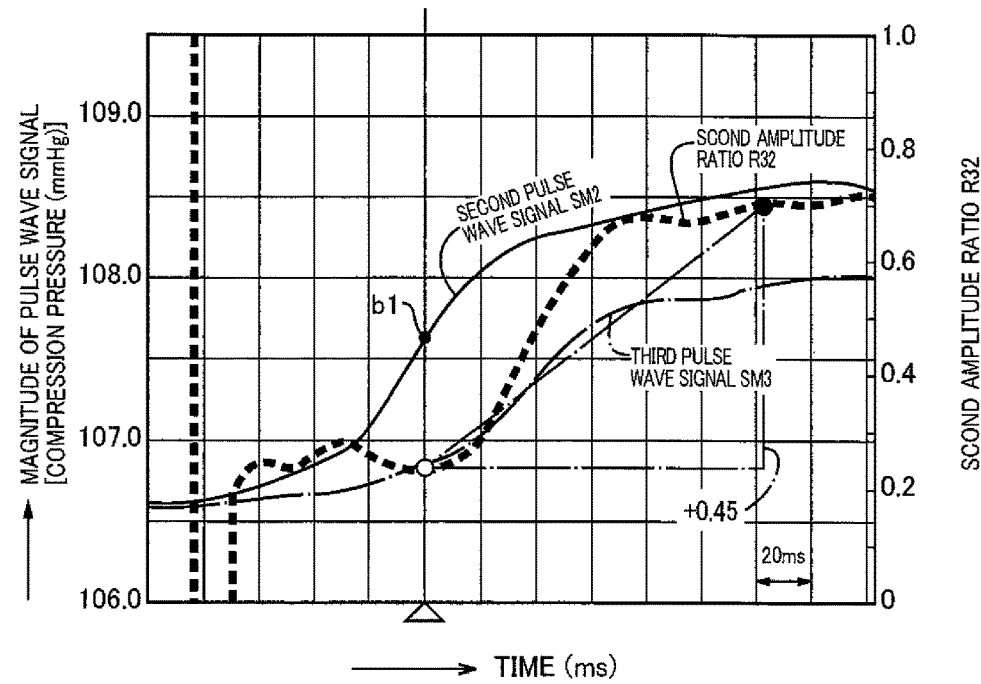
FIG. 26 is a diagram depicted on a time axis of the second pulse wave signal and the third pulse wave signal that is an example when the compression pressure of the compression band reaches the maximum blood pressure value, and the second amplitude ratio calculated from the signals.

After S6, at S7 corresponding to the maximum blood pressure value determining means 88, pulse wave data used for determining the maximum blood pressure value is limited to pulse wave data equal to or greater than a preset lower limit value such as greater than 100 mmHg, for example, and is limited to pulse wave data after the inflection point b1 of the first pulse wave signal SM1 within one pulse, i.e., the data depicted on the right side from the inflection point b1 in FIGS. 23 to 26 depicting actual data. FIG. 23 depicts the first pulse wave signal SM1 and the second pulse wave signal SM2 before the compression pressure of the compression band 12 reaches the maximum blood pressure value SBP and the first amplitude ratio R21 (=A2/A1) calculated from the signals; FIG. 24 depicts the second pulse wave signal SM2 and the third pulse wave signal SM3 before the compression pressure of the compression band 12 reaches the maximum blood pressure value SBP and the second amplitude ratio R32 (=A3/A2) calculated from the signals; FIG. 25 depicts the first pulse wave signal SM1 and the second pulse wave signal SM2 when the compression pressure of the compression band 12 reaches the maximum blood pressure value SBP and the first amplitude ratio R21 (=A2/A1) calculated from the signals; and FIG. 26 depicts the second pulse wave signal SM2 and the third pulse wave signal SM3 when the compression pressure of the compression band 12 reaches the maximum blood pressure value SBP and the second amplitude ratio R32 (=A3/A2) calculated from the signals.

At S8 corresponding to the maximum blood pressure value determining means 88, the amplitude values A1, A2, and A3 are calculated from the first pulse wave signal SM1, the second pulse wave signal SM2, and the third pulse wave signal SM3 read for each compression pressure. At S9 corresponding to the maximum blood pressure value determining means 88, the first amplitude ratio R21 (=A2/A1) and the second amplitude ratio R32 (=A3/A2) are calculated from the amplitude values A1, A2, and A3. At S10 corresponding to the maximum blood pressure value determining means 88, it is determined whether a rising width of the first amplitude ratio R21 after, for example, the inflection point b1 exceeds the first amplitude ratio change judgment value RR1 set to about 0.2, for example, and whether a rising width of the second amplitude ratio R32 after, for example, the inflection point b1 exceeds the second amplitude ratio change judgment value RR2 set to about 0.2, for example. Initially, since the compression pressure of the compression band 12 does not yet reach the maximum blood pressure value SBP, the rising width of the first amplitude ratio R21 after the inflection point b1 is about 0.05 and the rising width of the second amplitude ratio R32 after the inflection point b1 is about 0.05 as depicted in FIGS. 23 and 24 and, therefore, the determination of S10 is negative.

If the determination of S10 is negative as described above, S8 and later are repeatedly executed for the first pulse wave signal SM1, the second pulse wave signal SM2, and the third pulse wave signal SM3 corresponding to the next compression pressure. If the compression pressure of the compression band 12 reaches the maximum blood pressure value SBP while S8 to S10 are repeatedly executed, as depicted in FIGS. 25 and 26, the rising width of the first amplitude ratio R21 after the inflection point b1 abruptly increases to about 0.55 and the rising width of the second amplitude ratio R32 after the inflection point b1 abruptly increases to about 0.45 and, therefore, the determination of S10 becomes affirmative. If the determination of S10 becomes affirmative as described above, at S11, the compression pressure at the time of collection of the first pulse wave signal SM1, the second pulse wave signal SM2, and the third pulse wave signal SM3 used at this point is determined as the maximum blood pressure value SBP.

After S11, at S12 of FIG. 21 corresponding to the minimum blood pressure value determining means 90, the compression pressure range of the pulse wave data used for determining the minimum blood pressure value is limited to an upper limit value of about 100 mmHg or less, for example.

After S12, at S13 corresponding to the minimum blood pressure value determining means 90, a time ta1 of the rising point a1 of the first pulse wave signal SM1 is determined based on the first pulse wave signal SM1 from the upstream expansion bag 22 corresponding to a measurement point having the largest compression pressure value PC2 within the compression pressure range limited at S12. The time ta1 is the time after the start of the blood pressure measurement.

In the case of second or later S13, the time ta1 of the rising point a1 of the first pulse wave signal SM1 is determined based on the first pulse wave signal SM1 from the upstream expansion bag 22 corresponding to a measurement point having a smaller compression pressure value PC2 next to the compression pressure value PC2 of previous S15.

At S13 executed for the first time, a time ta2 of the rising point a2 of the second pulse wave signal SM2 is determined based on the second pulse wave signal SM2 from the intermediate expansion bag 24 at the measurement point having the largest compression pressure value PC2 within the compression pressure range limited at S12. The time ta2 is the time after the start of the blood pressure measurement. In the case of second or later S13, the time ta2 of the rising point a2 of the second pulse wave signal SM2 is determined based on the second pulse wave signal SM2 from the intermediate expansion bag 24 corresponding to the measurement point having a smaller compression pressure value PC2 next to the compression pressure value PC2 of previous S13.

At S13 executed for the first time, a time ta3 of the rising point a3 of the third pulse wave signal SM3 is determined based on the third pulse wave signal SM3 from the downstream expansion bag 26 at the measurement point having the largest compression pressure value PC2 within the compression pressure range limited at S12. The time ta3 is the time after the start of the blood pressure measurement. In the case of second or later S13, the time ta3 of the rising point a3 of the third pulse wave signal SM3 is determined based on the third pulse wave signal SM3 from the downstream expansion bag 26 corresponding to the measurement point having a smaller compression pressure value PC2 next to the compression pressure value PC2 of previous S13.

At S14 corresponding to the minimum blood pressure value determining means 90, the second time difference t21 (=ta2−ta1) is calculated from a difference between the time ta2 and the time ta1 and the first time difference t32 (=ta3−ta2) is calculated from a difference between the time ta3 and the time ta2, based on the times ta1 to ta3 determined at immediately preceding S13. The pulse wave propagation speed PWV is calculated by dividing the calculated first time difference t32 by the distance in the width direction between the intermediate expansion bag 24 and the downstream expansion bag 26, and the change rate $R_{PWV}$ of the pulse wave propagation speed PWV for the compression pressure value PC2 of the intermediate expansion bag 24 is then calculated from a slope of the tangent of the curve representative of a relationship between the pulse wave propagation speed PWV and the compression pressure value PC2 indicated in the two-dimensional coordinates of the compression pressure value axis and the pulse wave propagation speed axis as depicted in FIG. 18.

At S15 corresponding to the minimum blood pressure value determining means 90, it is determined whether the first time difference t32 is smaller than a preset time difference judgment value tc; the second time difference t21 is smaller than the time difference judgment value tc; and the change rate $R_{PWV}$ of the pulse wave propagation speed PWV is smaller than a preset change rate judgment value Rc in the area in which the change rate $R_{PWV}$ continuously increases as the compression pressure value PC2 increases from a lower limit value, for example, zero, as indicated by the arrow b in FIG. 18.

If the determination of S15 is negative, S13 and later are repeatedly executed. If the determination of S15 is affirmative, at S16 corresponding to the minimum blood pressure value determining means 90, the minimum blood pressure value DBP of the living body is determined by linear interpolation based on the compression pressure value PC2 of the intermediate expansion bag 24 corresponding to the second pulse wave signal SM2 used at immediately preceding S13 and a compression pressure value PC2' of the intermediate expansion bag 24 corresponding to a pulse wave signal SM2' used at S13 executed immediately before the immediately preceding S13.

At S17, the maximum blood pressure value SBP and the minimum blood pressure value DBP of the living body are displayed on the display device 78 and this routine is terminated.

As described above, according to the automatic blood pressure measuring apparatus 14 of this example, the compression band 12 has a plurality of expansion bags, i.e., the upstream expansion bag 22, the intermediate expansion bag 24, and the downstream expansion bag 26, having independent air chambers aligned in the width direction to respectively compress the upper arm 10 that is a compressed site of a living body, and when the first amplitude ratio change judgment value RR1 is exceeded by the first amplitude ratio R21 (=A2/A1) that is a ratio of the amplitude value A2 of the intermediate expansion bag 24 to the amplitude value A1 of the first pulse wave signal SM1 from the upstream expansion bag 22 and the second amplitude ratio change judgment value RR2 is exceeded by the second amplitude ratio R32 (=A3/A2) that is a ratio of the amplitude value A3 of the third pulse wave signal SM3 from the downstream expansion bag 26 to the amplitude value A2 of the second pulse wave signal SM2 from the intermediate expansion bag 24, the maximum blood pressure value SBP is determined based on the compression pressure at the time of acquisition of the first pulse wave signal SM1, the second pulse wave signal SM2, and the third pulse wave signal SM3 used at this point. Therefore, since the correct pulse wave signals SM are acquired by applying the compression pressure to the artery 16 of the upper arm 10 in uniform pressure distribution from the plurality of the expansion bags 22, 24, and 26 put into a mutually independent state in terms of pressure variation, the highly accurate maximum blood pressure value SBP is acquired based on the first amplitude ratio R21 and the second amplitude ratio R32 between the pulse wave signals SM. Since the first amplitude ratio R21 and the second amplitude ratio R32 have the property of abruptly increasing when the compression pressure of the compression band 12 nearly reaches the maximum blood pressure value SBP of the living body, the highly accurate maximum blood pressure value SBP can be acquired by judging the abrupt increase by using the amplitude ratio change judgment values RR1, RR2.

According to the automatic blood pressure measuring apparatus 14 of this example, since the compression band 12 has a pair of the upstream expansion bag 22 and the downstream expansion bag 26 consisting of flexible sheets positioned across a predetermined distance in the longitudinal direction of the compressed site, and the intermediate expansion bag 24 that is disposed between the upstream expansion bag 22 and the downstream expansion bag 26 to align in the longitudinal direction of the compressed site and that has an air chamber independent of the upstream expansion bag 22 and the downstream expansion bag 26, correct pulse waves are acquired by applying the compression pressure to the artery 16 in the compressed site of the living body in uniform pressure distribution from the upstream expansion bag 22, the intermediate expansion bag 24, and the downstream expansion bag 26 aligning in the longitudinal direction of the compressed site and put into a mutually independent state in terms of pressure variation and, therefore, the highly accurate maximum blood pressure value SBP is acquired based on the amplitude ratios, i.e., the first amplitude ratio R21 and the second amplitude ratio R32, between the pulse waves.

According to the automatic blood pressure measuring apparatus 14 of this example, in the process of reducing the compression pressure value of the pressurized compression band 12 while the compressed site is compressed at the same pressures by the upstream expansion bag 22, the intermediate expansion bag 24, and the downstream expansion bag 26, when the preset first amplitude ratio change judgment value RR1 is exceeded by the first amplitude ratio R21 that is a value acquired by dividing the amplitude value A2 of the second pulse wave signal SM2 from the intermediate expansion bag 24 by the amplitude value A1 of the first pulse wave signal SM1 from the upstream expansion bag 22 and/or the preset second amplitude ratio change judgment value RR2 is exceeded by the second amplitude ratio R32 that is a value acquired by dividing the amplitude value A3 of the third pulse wave signal SM3 from the downstream expansion bag 26 by the amplitude value A2 of the second pulse wave signal SM2 from the intermediate expansion bag 24, the compression pressure value of the intermediate expansion bag 24 is determined as the maximum blood pressure value SBP of the living body. Therefore, discrimination is made between a state in which the blood flow of the artery 16 in the compressed site passes under the upstream expansion bag 22 and does not pass under the intermediate expansion bag 24 and/or under the downstream expansion bag 26 and a state in which the blood flow of the artery 16 in the compressed site passes under both the intermediate expansion bag 24 and the downstream expansion bag 26 and, when the blood flow of the artery 16 in the compressed site starts passing under the upstream expansion bag 22 and under both the intermediate expansion bag 24 and/or the downstream expansion bag 26, the compression pressure value of the compression band 12 is determined as the maximum blood pressure value SBP of the living body and, thus, the highly accurate maximum blood pressure value SBP is acquired.

According to the automatic blood pressure measuring apparatus 14 of this example, in the process of reducing the compression pressure value of the pressurized compression band 12 while the compressed site is compressed at the same pressures by the upstream expansion bag 22, the intermediate expansion bag 24, and the downstream expansion bag 26, when the preset third amplitude ratio change judgment value RR3 is exceeded by the third amplitude ratio R31 that is a value acquired by dividing the amplitude value A3 of the third pulse wave signal SM3 from the downstream expansion bag 26 by the amplitude value A1 of the first pulse wave signal SM1 from the upstream expansion bag 22, the compression pressure value of the intermediate expansion bag 24 is determined as the maximum blood pressure value SBP of the living body. Therefore, discrimination is made between a state in which the blood flow of the artery 16 in the compressed site passes under the upstream expansion bag 22 and does not pass under the downstream expansion bag 26 and a state in which the blood flow of the artery 16 in the compressed site passes under both the upstream expansion bag 22 and the downstream expansion bag 26 and, when the blood flow of the artery 16 in the compressed site starts passing under the upstream expansion bag 22 and the downstream expansion bag 26, the compression pressure value of the intermediate expansion bag 24 in uniform pressure distribution in the width direction is determined as the maximum blood pressure value of the living body and, thus, the highly accurate maximum blood pressure value SBP is acquired.

According to the automatic blood pressure measuring apparatus 14 of this example, the pressure sensors T1, T2, and T3 detecting pressure in the plurality of the expansion bags 22, 24, and 26 are included and, after the compression pressure values PC of the expansion bags 22, 24, and 26 of the compression band 12 wrapped around the upper arm 10 are increased to a value sufficient for stopping a blood flow of the artery 16 in the upper arm 10, in the process of reducing each of the compression pressure values PC at the same time, the compression pressure values PC are retained for a predetermined time each time a predetermined amount of pressure within, for example, a range of 1 to 10 mmHg is gradually reduced to detect the first pulse wave signal SM1, the second pulse wave signal SM2, and the third pulse wave signal SM3 indicative of pulse waves that are compression oscillations in the upstream expansion bag 22, the intermediate expansion bag 24, and the downstream expansion bag 26 within the predetermined time and, therefore, since the first pulse wave signal SM1, the second pulse wave signal SM2, and the third pulse wave signal SM3 are detected when the compression pressure values PC are constant, the correct pulse wave signals SM1, SM2, and SM3 can be acquired. If a plurality of pulse waves are detected within the predetermined time and the maximum blood pressure value is determined based on an average value of the plurality of the pulse waves, the more highly accurate maximum blood pressure value is acquired.

According to the automatic blood pressure measuring apparatus 14 of this example, the amplitude value A1 of the pulse wave from the upstream expansion bag 22, the amplitude value A2 of the pulse wave from the intermediate expansion bag 24, and the amplitude value A3 of the pulse wave from the downstream expansion bag 26 are sequentially acquired within one pulse of the living body in the sampling periods shorter than a period of the pulse and the amplitude ratios R21, R32, and R31 are sequentially calculated from the amplitude value A1 of the pulse wave from the upstream expansion bag 22, the amplitude value A2 of the pulse wave from the intermediate expansion bag 24, and the amplitude value A3 of the pulse wave from the downstream expansion bag 26 sequentially acquired in the sampling periods shorter than the period of the pulse, the highly accurate maximum blood pressure value is acquired, based on the amplitude ratios R21, R32, and R31 sequentially obtained within one pulse, by judging the abrupt increase thereof by using the amplitude ratio change judgment values RR1, RR2, and RR3.

Although one example of the present invention has been described in detail with reference to the drawings, the present invention is not limited to this example and is also implemented in other forms.

For example, the pressurization target pressure value PCM and the measurement termination pressure value PCE may not necessarily be set. For example, based on the maximum blood pressure value SBP and the minimum blood pressure value DBP of the previous measurement input by an operator after turning on of the power switch of the automatic blood pressure measuring apparatus 14, the pressurization target pressure value PCM may be set to a value acquired by adding a predetermined value (e.g., 30 mmHg) to the input maximum blood pressure value SBP and the measurement termination pressure value PCE may be set to a value acquired by subtracting a predetermined value (e.g., 30 mmHg) from the input minimum blood pressure value DBP. Alternatively, during rapid pressure increase (between times t1 and t2 of FIG. 18) by the cuff pressure control means 82, for example, the pulse wave signal SM2 from the intermediate expansion bag 24 may be extracted to create an envelope and the maximum blood pressure value SBP and the minimum blood pressure value DBP of the living body may be predicted in accordance with a well-known oscillometric algorithm based on the envelop to set the pressurization target pressure value PCM to a value acquired by adding a predetermined value (e.g., 20 mmHg) to the predicted maximum blood pressure value SBP and to set the measurement termination pressure value PCE to a value acquired by subtracting a predetermined value (e.g., 20 mmHg) from the predicted minimum blood pressure value DBP.

While the compression pressure values PC of the expansion bags 22, 24, and 26 are retained for a predetermined time in the gradual pressure reduction process by the cuff pressure control means 82, the amplitude value determining means 84 may collect the pulse wave signals SM1, SM2, and SM3 from the expansion bags 22, 24, and 26 for a plurality of pulses, and the maximum blood pressure value SBP and the minimum blood pressure value DBP may be determined based on the average value of the pulse wave signals SM for the plurality of pulses. In this case, the more highly accurate blood pressure value is acquired.

When a blood pressure is measured, after a pressure increase to the pressurization target pressure value PCM, the compression pressure values PC may not necessarily be reduced stepwise at a preset gradual pressure reduction speed. In other words, the compression pressure values PC may continuously be reduced. The gradual pressure reduction may be performed only around the blood pressure measurement and the rapid pressure reduction may be performed in the other sections to shorten a measurement time.

Although pressure reduction measurement is performed to determine a blood pressure value in the process of reducing the compression pressure of the compression band 12 in the example, this is not a limitation and pressure increase measurement may be performed to determine a blood pressure value in the process of increasing the compression pressure of the compression band 12. The maximum blood pressure value determination algorithm and the minimum blood pressure value determination algorithm described above can also be used in such pressure increase measurement and the same effects can be obtained.

The number of the expansion bags included in the compression band 12 is not limited to three and may be four or more.

In the example, from the amplitude values A1, A2, and A3 of the mutually synchronized pulse wave signals SM1, SM2, and SM3, the amplitude values A1, A2, and A3 are sequentially determined within one pulse in sampling periods sufficiently shorter than a pulse period, for example, in periods of a few milliseconds to a few tens of milliseconds, to calculate the first amplitude ratio R21 (=A2/A1), the second amplitude ratio R32 (=A3/A2), and the third amplitude ratio R31 (=A3/A1) from the amplitude values A1, A2, and A3, and the maximum blood pressure value SBP is determined based on that the first amplitude ratio R21 exceeds the preset first amplitude ratio change judgment value RR1 and/or that the second amplitude ratio R32 exceeds the preset second amplitude ratio change judgment value RR2 or that the third amplitude ratio R31 exceeds the preset third amplitude ratio change judgment value RR3. However, to increase changes in the first amplitude ratio R21

(=A2/A1), the second amplitude ratio R32 (=A3/A2), or the third amplitude ratio R31 (=A3/A1) to facilitate the judgment at the time of determination of the maximum blood pressure, the amplitude value A2 or A3 of the pulse wave signal SM2 or SM3 generated after the pulse wave signal SM1, for example, at the next pulse, may be used for obtaining the amplitude ratios.

The above description is merely an embodiment and, although not exemplarily illustrated one by one, the present invention may be implemented in variously modified and improved forms based on the knowledge of those skilled in the art without departing from the spirit thereof.

NOMENCLATURE OF ELEMENTS

10: upper arm (compressed site) 12: compression band 14: automatic blood pressure measuring apparatus 16: artery 22: upstream expansion bag 24: intermediate expansion bag (upstream expansion bag or downstream expansion bag) 26: downstream expansion bag A1,A2, A3: amplitude value PC1, PC2, PC3: compression pressure value RR1: first amplitude ratio change judgment value RR2: second amplitude ratio change judgment value SBP: maximum blood pressure value (blood pressure value) SM1, SM2, SM3: pulse wave signal (pulse wave) T1: first pressure sensor T2: second pressure sensor T3: third pressure sensor R21: first amplitude ratio (amplitude ratio) R32: second amplitude ratio (amplitude ratio)

The invention claimed is:

1. An automatic blood pressure measuring apparatus comprising: a compression band wrapped around a compressed site of a living body, the automatic blood pressure measuring apparatus sequentially extracting a pulse wave that is pressure oscillation in the compression band in a process of changing a compression pressure value of the compression band to determine a blood pressure value of the living body based on a change in the pulse wave,
the compression band having a plurality of expansion bags having independent air chambers aligned in a width direction to respectively compress the compressed site of the living body,
the automatic blood pressure measuring apparatus having a processor configured to:
sequentially calculate within one pulse period, amplitude ratios of an amplitude value of a downstream pulse wave from a predetermined expansion bag positioned on a downstream side of an upstream expansion bag positioned on an upstream side of an artery in the compressed site out of the plurality of the expansion bags to an amplitude value of an upstream pulse wave from the upstream expansion bag, the automatic blood pressure measuring apparatus determining a maximum blood pressure value of the living body based on whether the amplitude ratios exceed a preset amplitude ratio change judgment value that is defined in advance for judging a rise of the amplitude ratios at a start of a blood flow,
wherein the amplitude value of the upstream pulse wave from the upstream expansion bag and the amplitude value of the downstream pulse wave from the downstream expansion bag are sequentially acquired in periods within one pulse of the living body and shorter than a period of a pulse,
wherein the amplitude ratios are sequentially calculated in periods shorter than the period of the pulse from the amplitude value of the upstream pulse wave from the upstream expansion bag and the amplitude value of the downstream pulse wave from the downstream expansion bag sequentially acquired in periods shorter than the period of the pulse; and
determining, for each pulse wave, whether the amplitude ratios sequentially calculated within the one pulse period from the amplitude value of the upstream pulse wave from the upstream expansion bag and the amplitude value of the downstream pulse wave from the downstream expansion bag sequentially acquired within the each pulse wave exceeds the preset amplitude ratio change judgment value, and using the determination to thereby estimate the maximum blood pressure value of the living body.

2. The automatic blood pressure measuring apparatus of claim 1, wherein
the compression band has a pair of the upstream expansion bag and the downstream expansion bag comprised of flexible sheets positioned across a predetermined distance in a longitudinal direction of the compressed site, and an intermediate expansion bag disposed between the upstream expansion bag and the downstream expansion bag to align in the longitudinal direction of the compressed site, and wherein the intermediate expansion bag has an air chamber independent of the upstream expansion bag and the downstream expansion bag.

3. The automatic blood pressure measuring apparatus of claim 2, wherein
in a process of reducing a compression pressure value of the pressurized compression band while the compressed site is compressed at same pressures by the upstream expansion bag, the intermediate expansion bag, and the downstream expansion bag, when a preset first amplitude ratio change judgment value is exceeded by a first amplitude ratio that is a value acquired by dividing an amplitude value of an intermediate pulse wave from the intermediate expansion bag by the amplitude value of the upstream pulse wave from the upstream expansion bag and a preset second amplitude ratio change judgment value is exceeded by a second amplitude ratio that is a value acquired by dividing the amplitude value of the downstream pulse wave from the downstream expansion bag by the amplitude value of the intermediate pulse wave from the intermediate expansion bag, the maximum blood pressure value of the living body is determined based on a compression pressure value of the intermediate expansion bag.

4. The automatic blood pressure measuring apparatus of claim 2, wherein
in a process of reducing a compression pressure value of the pressurized compression band while the compressed site is compressed at same pressures by the upstream expansion bag, the intermediate expansion bag, and the downstream expansion bag, when a preset third amplitude ratio change judgment value is exceeded by a third amplitude ratio that is a value acquired by dividing the amplitude value of the downstream pulse wave from the downstream expansion bag by the amplitude value of the upstream pulse wave from the upstream expansion bag, the maximum blood pressure value of the living body is determined based on a compression pressure value of the intermediate expansion bag.

5. The automatic blood pressure measuring apparatus of claim 1, comprising pressure sensors detecting pressure in the plurality of the expansion bags, wherein after a compression pressure value of the plurality of the expansion bags of the compression band wrapped around the compressed site is increased to a value sufficient for stopping a blood flow of an artery in the compressed site, in a process of reducing the compression pressure value of the compression band, the automatic blood pressure measuring apparatus retains the compression pressure value of the compression band for a predetermined time each time a predetermined amount of pressure is gradually reduced and detects the pulse wave that is pressure oscillation in the compression band within the predetermined time.

6. The automatic blood pressure measuring apparatus of claim 1, wherein the maximum blood pressure value of the living body is determined to correspond to a pressure at a time that the rise is judged.

* * * * *